US005803082A

United States Patent [19]
Stapleton et al.

[11] Patent Number: 5,803,082
[45] Date of Patent: Sep. 8, 1998

[54] OMNISPECTRAMAMMOGRAPHY

[75] Inventors: John J. Stapleton; Barbara K. Stapleton, both of New Brunswick; Raymond W. Saxon, Jr., Beach Haven, all of N.J.

[73] Assignee: Staplevision Inc., East Brunswick, N.J.

[21] Appl. No.: 843,731

[22] Filed: Apr. 21, 1997

Related U.S. Application Data

[63] Continuation of Ser. No. 615,791, Mar. 14, 1996, abandoned, which is a continuation of Ser. No. 150,444, Nov. 9, 1993, abandoned.

[51] Int. Cl.$^6$ ............................................. A61B 6/00
[52] U.S. Cl. ...................... 128/653.1; 128/664; 128/665; 607/89
[58] Field of Search .................................. 128/633, 634, 128/653.1, 664, 665; 250/339.01, 339.09, 339.11, 339.12, 341.1, 341.5, 341.8; 607/88, 89

[56] References Cited

U.S. PATENT DOCUMENTS 5,007,428   4/1991   Watmough .............................. 128/664
5,293,873   3/1994   Fang ....................................... 128/664

Primary Examiner—Ruth S. Smith
Attorney, Agent, or Firm—Kane, Dalsimer, Sullivan, Kurucz, Levy, Eisele and Richard, LLP

[57] ABSTRACT

An omnidirectional, multispectral and multimodal sensor/display processor for the screening, examination, detection, and diagnosis of breast cancer. Its capabilities are accomplished through stable vision fusion of the Doppler-like differences of selective radiologic wavelengths, besides X-ray mammograms, e.g., ultraviolet (UV.), visible and infrared (IR), with-vision-computer discrimination of other active and passive observables of electromagnetic fields, and medical data, including the optimum color ratios and 3-dimensional (3D) transformation of multiple imaging modalities, e.g., ultrasound, nuclear computed tomography (CT), magnetic resonance imaging (MRI), etc., to obtain the "concurrence of evidence" necessary for maximum confidence levels, generated at minimal cost and with minimum false positives, at the earliest possible breast cancer detection point.

14 Claims, 13 Drawing Sheets

OMNISPECTRAMAMMOGRAPHY

This is a continuation of application Ser. No. 08/615,791 filed on Mar. 14, 1996, now abandoned, which is a continuation of application Ser. No. 08/150,444 filed Nov. 9, 1993, now abandoned.

FIELD OF THE INVENTION

The present invention is directed towards a sensor/display processor and methodology therefore of multispectral, multimodal medical imaging for screening and diagnostic purposes.

BACKGROUND OF THE INVENTION

The present invention relates to the medical adaptation of Omnispectravision as described in U.S. Pat. Nos. 4,343,020 and 4,418,359, and an expanded application of automated quality assurance, U.S. patent application Ser. No. 965,625 and filed Oct. 22,1992, the disclosures of which are incorporated herein by reference.

There presently exists an ever expanding need for much earlier detection, and more accurate diagnosis and treatment of breast cancer, an ancient dread disease, because more than 46,000 women die from it this year (1993) and another 180,000 new cases will be detected here in the United States alone. Evidently, there is no single cause of breast cancer and, since its etiology is complex and obscure, the X-ray mammogram remains the singular modality approved for use in breast cancer screening despite well known deficiencies and ambiguities.

About 70–75% of all breast cancers originate in ductal epithelium and most of the rest originate in lobular epithelium. Significantly in these conduits of milk, the inventors noted the metabolic energy density of milk happens to equal the average daily energy density expended by breast cancer with its average doubling times (growth rate) of 100 days that is inversely proportional to its power density and such energy expenditure. See FIGS. 2 and 4.

The breast appears relatively disordered in its complexity, lacking uniform architectural landmarks . . . "The inhomogeneities found in varying degrees in all breasts compromise the ability of imaging studies to detect the early epithelia changes that may indicate a malignant process." [Kopans D B, *Breast Imaging*, J. B. Lippincott Co., Philadelphia, Pa., 1989, hereinafter, Kopans 1.]

With regard to the breast's inhomogeneities, those visual inhomogeneities, other than spatial and temporal, are defined as color and, thus, multispectral observables need to be properly transformed to color ratios which in turn tightly cluster the cancer datapoints and separate them from the clutter of benign conditions or other disease. Unfortunately, pseudo-color thermography added cost and confusion, rather than fusion of observables, and was deemed (in 1976 when thermogenesis was poorly understood) "not an adequate screening method for detection of breast cancer or other breast disease when used alone or with only a physical examination". [Kopans 1.]

In addition, "Virtually every aspect of breast cancer detection and therapy is fraught with controversy . . . "[Kopans 1.] because each modality alone is qualitative, subjective and anecdotal, with great variation in results. Accordingly, "It is especially important that additional research be undertaken to determine the nature of tumor thermogenesis" [Bassett L H, *Mammography, Thermography, and Ultrasound in Breast Cancer Detection,* Grune and Stratton, New York, N.Y., 1982, hereinafter, Bassett 1.] and there exists a need for a comfortable, low cost, personal screening sensor/display, augmented by fusion of sophisticated synergism from the best data produced by each radiologic modality. [Strax P, *Make Sure You Do Not Have Breast Cancer,* St. Martin's Press, New York, N.Y. 1989, hereinafter, Strax 1.]

SUMMARY OF THE INVENTION

It is a principle objective of this invention to provide multispectral, multimodal UV-IR imaging spectroscopy and enabling technology for women to screen and for doctors to diagnose changes within breast anatomy for the earliest detection of cancer. It is a further objective to provide for the optimum effective use of vision-computers for clues to the causes and cure of cancer and, thereby, maximize confidence and minimize false alarms, fears and costs in order to encourage screening.

The present invention provides for earlier breast cancer detection calmly. This is accomplished by such adaptation and optimization of prior technology which will enable women (and their physicians) to actually see changes within their own breast anatomy in less than half the 27–30 cancer cell doubling-times of present mammographic diagnostic and palpability screening. It can be said that women's breasts conduct and radiate adaptive thermal observables and OMNISPECTRAMAMMOGRAPHY sees and accurately transforms the 3D information of screened breast anatomy for visualization on low-cost displays. This capability could save thousands of women's lives in the very near term; it's called Calm Look Care, where such a "look" will take only 10 to 114 seconds.

To screen for and definitively detect the earliest (smallest) pre-cancerous breast conditions, i.e., hyperplasia with atypia and carcinoma in situ, requires a new, higher confidence, multimodal, omnidirectional, multispectral, dynamic vision—a product capable of "seeing the invisible". OMNISPECTRAMAMMOGRAPHY provides such vision, enabling physicians to detect the presence of the earliest cancer—like cell growth, to pinpoint, as it were, its precise positioning, and to see its propagation through the presentation of the many variables of observable parameters inherent within complex breast anatomy. The breast's anatomy, as sources of diffusivity, thermal conductivity, specific heat and specific gravity (density), and with transreflective transillumination is adaptively processed and presented as a video "picture" with an internal clarity well beyond that presented by present day x-ray absorption and scattering coefficients. $[\Sigma \sigma_I = -\text{Ln (Transferance)}/\text{Depth} = 2.3 \text{ Density/Depth}]$.

The observable energy density expended per day by atypical cell growth within breast anatomy equals 727 calories/cc, and the average volume doubling-time of such growth is 100 days which is inversely proportional to its power density from rapid, to average, to slow growth. Thus, practical detection of one additional cell growth $2^{15}$ to $2^{15}+1$ in 1.9 to 19.0 minutes and from 1 to 2 in 30–300 days because 30 days * 120 mw/cc=100 days * 36 mw/cc=300 days * 12 mw/cc, as shown in FIG. 4.

OMNISPECTRAMAMMOGRAPHY's 3D digital radiography is effectively a multicolor, omnidirectional, computer axial tomography (CAT) scan, utilizing over 300,000 optical fibers and discrete detectors. Its practical visualization is provided with automated quality assurance and a "concurrence of evidence" enhancing existing modalities, and is affordable due, in part, to the development of single integrated circuit (1-IC) sensors. These sensor's focal plane arrays of discrete optical detectors of energy, from ultraviolet through the visible and infrared ranges, expands five octaves of "visual vibrations" [(380–760 nm) * 0.5, 1, 2, 4, 8], such that the mind's eye magenta-Doppler effect (as discussed more fully hereinafter,) can detect minute (1 ppm=$10^{-6}$) changes in realtime. Correlations of this information, over periodic intervals, portend realistic goals of a 0.01 ppm=$10^{-8}$ false positive (alarm) rate and a 99.99% probability of detection rate (0.01% false negatives). Refer to FIG. 7 for a graphic presentation of these five octaves and FIG. 9 for a presentation of the magenta Doppler effect.

Analysis of needle probe data graphically shows normal and abnormal thermal gradients of breast anatomy, i.e., temperature differences over the various depths, and its thermal conductivity increases from 3 to 5.1 mw/cm° C. in the vicinity of a mass of atypical cell growth. See FIGS. 3A, 3B and 3C. The surface radiation and convection re-presents the in-depth heat transferance that is actually higher than the cancer power/area subsurface equivalent of nonlinear blackbody discriminants (Cp/a-bb). Since power density equals the product of gradients ($\nabla$) in thermal conductivity and temperature (dTC/dD*dT/dD), the leading and trailing edges, not unlike the "Mach bands" of the eyes and video's so-called "unsharp masking" [Laplacian $\nabla^2$, give edge-enhancement and multispectral point-extraction ($\nabla^4$). Today's computer power permits discrete signal processing techniques to resolve a picture element of about 0.3 mm and a volume element (a voxel) of $(0.3 \text{ mm})^3$ or 27 microcubic centimeters. Each detector of a 640×480 array is a nominal 25 microns of UV-IR PtSi CCDs. Its noise equivalent power of 82 femtowatts may ultimately discriminate the very first cell doubling from 1 to 2 cells, i.e., 12 pw/$(10 \mu)^3$.

BRIEF DESCRIPTION OF DRAWINGS

By the present invention, its objects and advantages will be realized, the description of which should be taken in conjunction with the drawings herein.

DETAILED DESCRIPTION OF THE PREFERRED EMBODIMENTS

Figure 1:
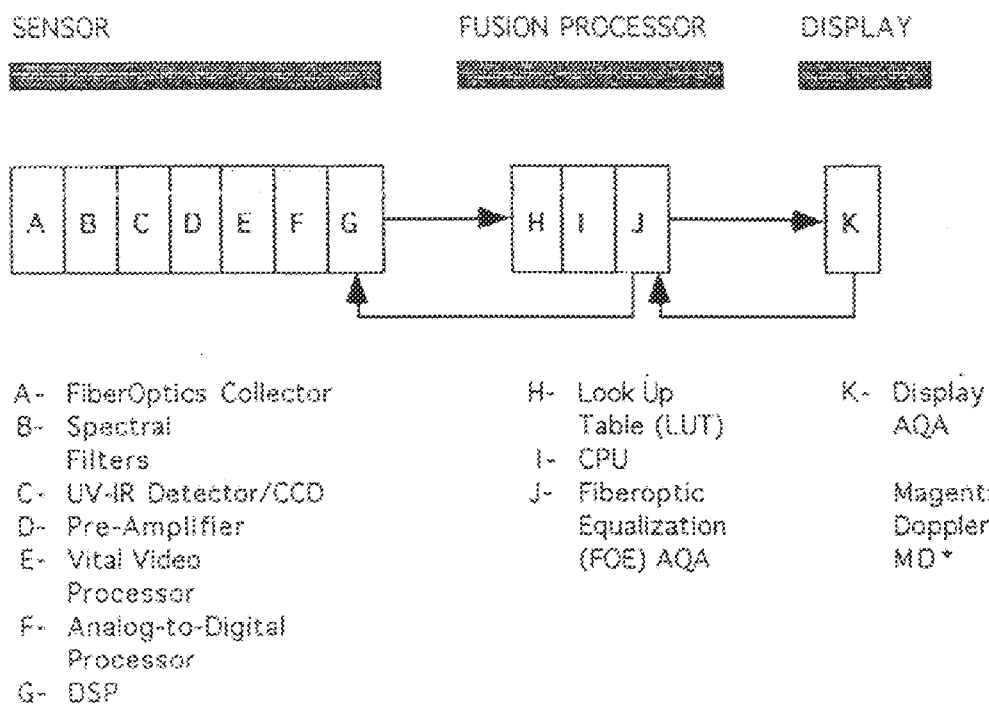
FIG. 1 shows a functional diagram of the invention—the Multispectral Sensor/Display Processor.

The present invention utilizes the adaptation of Omnispectravision [Stapleton J J, "Omnispectravision," U.S. Pat. Nos.: 4,343,020 and 4,418,359, Issued: 03 Aug. 1982 and 29 Nov. 1983, respectively, hereinafter, Stapleton 2] and associated technologies [Kraushaar R J, Mays R and Stapleton J J, "Single Sensor Spectrometer with High Spatial and Temporal Resolution," U.S. Pat. No. : 4,304,491, Issued: 08 Dec. 1981, hereinafter, Kraushaar, et al, 1, Stapleton J J, "LED/CCD Multiplexor and Infrared Image Converter," U.S. Pat. No. : 4,338,627, Issued: 06 Jul. 1982, hereinafter, Stapleton 1, & Stapleton J J, "Versatile Video CRT Display," U.S. Pat. No. : 4,361,785, Issued: 30 Nov. 1982, hereinafter, Stapleton 3, and Stapleton J J and Lord C, "An Automated Quality Assurance Image Processing System," U.S. patent application Ser. No.: 416,377, Filed: 03 Oct. 1989 and allowed 11 Jan. 1995, hereinafter, Stapleton, et al , 1, & Stapleton J J and Stapleton B K, "Large Thin Display," U.S. Pat. No. : 5,019,807, Issued: 28 May 1991. This invention—LTD—was reviewed in Tom Williams' article entitled "Coming Soon: Flexible Film in Large, Flat Displays" in the Jun. 1, 1989 issue of *Computer Design*, hereinafter, Stapleton, et al, 2] which will enable women (and their physicians) to actually see changes within their own breast anatomy in less than half the 27–30 cancer cell doubling-times of present mammographic technology and palpability techniques, respectively. It can be said that women's breasts conduct and radiate adaptive thermal observables and OMNISPECTRAMAMMOGRAPHY sees and accurately transforms thermal diffusivity 3D information for visualization on low-cost television displays and eventually through high-definition television (HDTV), as well. This capability could save thousands of women's lives, it's called Calm Look Care or simply CLC.

In its Revised Edition in 1989, *The Columbia University College of Physicians and Surgeons Complete Home Medical Guide* reported that breast cancer "remains the most common form of the disease among women, accounting for 142,000 new cases each year and about 43,000 deaths". These figures indicate "about 1 out of every 11 women will develop breast cancer" in her lifetime. Now just three years later, the numbers have sharply increased to a point where now 1 woman in 8 will develop cancer at some point in her life. [Harkin T (U.S. Senator, Iowa) in a November 4th letter "To the Editor" published in the *The New York Times* on Nov. 29, 1992, defended his "backdoor solution" to provide funding for breast cancer research, indicated that 180,000 women would develop breast cancer in 1992 and 46,000 women's lives would be taken [that] year alone—one every 12 minutes—from this disease, hereinafter, Harkin 1.] The cause of breast cancer is unknown but what is known is that early detection and treatment are essential in curing any form of cancer. "About 90% of localized breast cancer is now cured", according to this medical guide, "compared with 50 to 70 percent 5-year survival for more advanced disease." For breast cancer screening, the American Cancer Society now urges that all women have a baseline mammogram between the ages of 35 and 39, then have additional mammograms every 1–2 years from ages 40–49 and then on an annual basis thereafter. This is a change from their earlier recommendation for annual mammograms only for women over 50 or for women in high risk categories, suggesting the analysis of breast cancer data indicated large numbers of women in their forties can benefit from earlier screening. However, the results of the Canadian National Breast Screening Study, released early in November 1992 and discussed by CNN on it's November 11th MorningNews program, suggest such screening does not improve the breast cancer death rate for women at ages earlier than 50. The answer to CNN's question, "Is the screening test for breast cancer failing to tell women what they want to know?", appears to be at best ambiguous and more probably "Yes!". During the CNN program, Dr. Gillian Newshead, Assistant Professor of Radiology and Director of Breast Imaging at the New York University Medical Center, indicated the results of such earlier screenings are best when the radiology involved produces superb results and suggests the screening organizations be checked for accreditation by the American College of Radiology. Early detection is a common goal all involved seem to agree upon, and clearly it is most important for the woman at risk. Focus, therefore, should undoubtedly be directed at earlier detection and earlier care.

Heretofore, thermography, which involves measuring minute variations in heat generated by various body tissues, was studied as a breast cancer screening device. The idea is that cancer generates more heat than normal tissue; therefore, the detection of these so-called hot spots within the breast would raise suspicion of cancer. So far, the application of thermographic breast screening procedures has proved limited by positional and tonal confusions, and the difficulties associated with the non-visible thermal wave range and the ability to dynamically adjust to changes in these invisible ranges. (Monochrome thermammography reportedly had false negatives [misses] comparable to mammography but more false positives (alarms) due to clutter and contrast confusions of positional, tonal, and thermal parameters.) Nevertheless, breasts do conduct and radiate thermal waves of varying lengths dependant upon tissue densities and source distances, and any abnormal variations in such tissue; that is, since breasts conduct and radiate adaptive thermal vision, women can be afforded a Calm Look and early Care facility which produces useable results at a time when something can in fact be done without disrupting or threatening her life.

The fiberoptic equalization (FOE), employed in automatic quality assurance (AQA) [Stapleton, et al, 1.], enables the collection and feedback of information in order to control the invisible (to the naked eye) observables of ultraviolet-infrared image processing. Coupled with the demilitarization of certain infrared imaging technologies which originally lead to medical thermography, the concept of fiberoptic equalization can be utilized to enable breast cancer screening procedures to detect breast anomalies at a substantially earlier point in the breast cancer life cycle than heretofore thought possible. See FIG. 9.

Now, FOE permits computer calibrated color densities of both sensor and display, so that "Doppler differences" can readily and reliably be discerned amidst the natural dynamic range of environmental changes. A true-color imaging spectroscopy IC enhances IR CCD's Detectivity/Capacitance D*/C and Noise Equivalent Exposure (NEE) signal-to-noise figures of merit versus discrete InSb or HgTe.

A just noticeable difference of $<10^{-6}$ or 1-part-per-million is needed and is realizable now by $0.01^3$ stable sensitivity [deltas] in hue, saturation and value (dH, dS, and dV).

Of course, the emittance and reflectance, and breast anatomy transmittance also vary nonlinearly with wavelength (X), as does the foreground thermal conductivity, transmittance and detectors' figure of merit, D-star ($D_x^*$), diffraction limited optics spot size [Diam=$2.44*X*F_\#$] and optics chromatic "aberration".

Background Problems and Solutions regarding Breast Anatomy

The present invention approach, reverses the normally cogent method of input to output reasoning to the nonlinear synergism optimizing the sensor/display to perform as a workstation. Simply, this suggests the mind's eye, that is, the eye-brain's understanding of images dictates what is seen and the technology system must adapt to the environment as it exists. Over the years, the inventors have placed this research philosophy first in their responses to both military and civilian imaging requirements.

The logical conclusion of being affordable and reasonable in thermal imaging is shown in the so called D-star/

Capacitance and NEE should markedly out-perform present 1, 2 and 3 color UV-IR MIL/MED sensors, notwithstanding, apparent thermography deficiencies.

A number of important factors present themselves when attempting to apply the technologies of Omnispectravision to the thermodynamics of breast anatomy. A number principles of the modalities pertaining to military threat warning systems and medical imaging systems have been incorporated within the technology of OMNISPECTRAMAMMOGRAPHY to correct the individual shortcomings of each, producing a new visualization process IR to X-rays. Some of the more important of these factors (myths and counter-intuitive truths) are presented below:

1. Skin is opaque to infrared radiation. Fact: Heat is emitted, reflected, transmitted, absorbed, conducted and conveyed by convection through skin and its spectral reflectivity drops from 50 percent to 5 percent between 0.5 and 2.0 micron ($\mu$). [Fujimasa, et al, 1.] Even more colorfully from 0.76 to 2.00$\mu$. [Stolwijk 1.] Skin 1 mm thick transmits useful IR-color of 1.0% between 1.0–1.5$\mu$, of 0.5% at 0.5 $\mu$ and at 2.0$\mu$, and 0.25% at 2.5$\mu$. [Hardy J D in a paper entitled "The Radiatiing Power of Human Skin in the Infra-Red" and referenced by Fujimasa, et al, 1, above, 1939, hereinafter, Hardy 1.] See FIGS. 5 and 6A, and 6B and 6C.

2. Skin is not transparent. Fact: Transillumination (diaphanography) shows cancers tend to transmit more (of the lamps of) near-IR than the visible range. Skin 5 mm thick transmits 14 percent of 0.86$\mu$ and 20 percent of 1.13$\mu$. Tissue and vascular changes are clearly recognized but subtle abnormalities may be detected only by comparison of color of two breasts. [Isard H J in a paper entitled "Breast Thermography—The Mammatherm", presented at a June 1975 John Hopkins Hospital seminar on Medical Thermography, and published in *Medical Thermography, Theory and Clinical Applications* by the Brentwood Publishing Corp., Los Angeles, Calif. 1976, hereinafter, Isard 1.] Now, the 1-IC technology of OMNISPECTRAMAMMOGRAPHY bridges the gap between X-rays and UV-IR with its PtSi CCD. (The UV sensitivity of the PtSi CCD may ultimately assist in the analysis of resonance with UV-causing skin cancers and establish a potential correlation with the apparent higher incidence of sun bathers and breast cancers among certain groups of women.)

3. Skin temperature normally varies [dT/dtime]. The normal difference in skin temperature (of 0.7° C. between 4 am and 4 pm) obscures the detection of abnormal skin temperature. Actually, skin with a dT+2° C. from its normal (other) 33° C. is even greater in its depth. [Gautherie 1.] Monthly mean minimum and maximum skin temperatures are 33.9° C. to 34.9° C. (92.5% to 95.5% of oral temperature). [Simpson H W, Wilson D, Griffiths K, Mutch F, Halberg F, and Gautherie M in a paper entitled "Thermorhythmometry of the Breast: A Review to 1981", presented to the International Symposium on Biomedical Thermology, Strasbourg, France in 1981, and published in *Progress in Clinical and Biological Research, Volume 107: Biomedical Thermology* by Alan R. Liss, Inc. New York, N.Y., 1982, hereinafter, Simpson, et al, 1.] The desired NETs (Noise Equivalent Temperatures) of 0.1° C. means that a signal/noise ratio of 10/1 at a 1° C. threshold should have given much lower false alarm rate (FAR). Clutter and nongaussian noise components require several discriminations besides dT to lower FAR and threshold so as to reduce its 7–28% false negatives (misses). The PtSi CCD's NEE is $2^{-20}=10^{-6}=-120$ db below saturation, i.e., 40–60 db better than thermography. "As a homeotherm, man maintains a stable deep body temperature within relatively narrow limits ($37\pm1°$ C.) even though the environment may fluctuate widely."

At rest, the minimal metabolic rate is 45 w/sqm: warm blood flowing through the venous networks show surface temperature gradients within 7 mm of skin and smaller and wider gradients when deeper. "Thermography depicts these (superficial) veins in addition to deeper vessels, focal areas of infrared emission, global heat and alterations in breast contour." [Isard H J in a paper entitled "Breast Disease and Correlation of Images: Mammagram—Thermography—Diaphanography", presented to the International Symposium on Biomedical Thermology, Strasbourg, France in 1981, and published in *Progress in Clinical and Biological Research, Volume 107: Biomedical Thermology* by Alan R. Liss, Inc. New York, N.Y., 1982, hereinafter, Isard 2.]

Figure 3A:
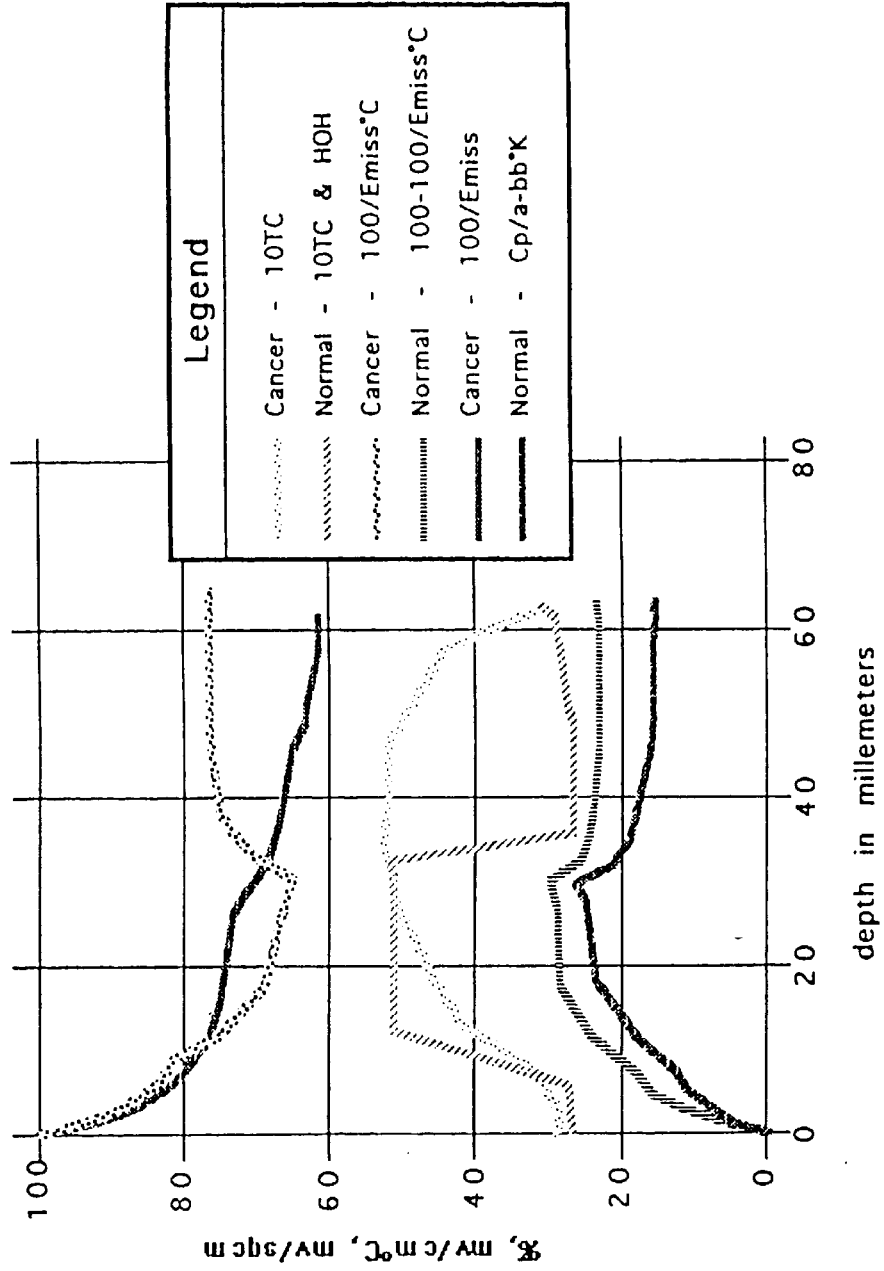
FIG. 3A shows a consolidation of cancer conductivity and emissivity analyses of the works of Gautherie, Berger, and others. [Berger G S and Keith L G in a paper entitled "Screening for Breast Cancer and Cost-Effectiveness of Thermal Diagnostic Techniques", presented to the International Symposium on Biomedical Thermology, Strasbourg, France in 1981, and published in *Progress in Clinical and Biological Research, Volume* 107: *Biomedical Thermology* by Alan R. Liss, Inc. New York, N.Y., 1982, hereinafter, Berger 1; and Gautherie M in a paper entitled "Temperature and Blood Flow Patterns in Breast Cancer During Natural Evolution and Following Radiography", presented to the International Symposium on Biomedical Thermology, Strasbourg, France in 1981, and published in *Progress in Clinical and Biological Research, Volume* 107: *Biomedical Thermology* by Alan R. Liss, Inc. New York, N.Y., 1982, hereinafter, Gautherie 1.]
Figure 3B:
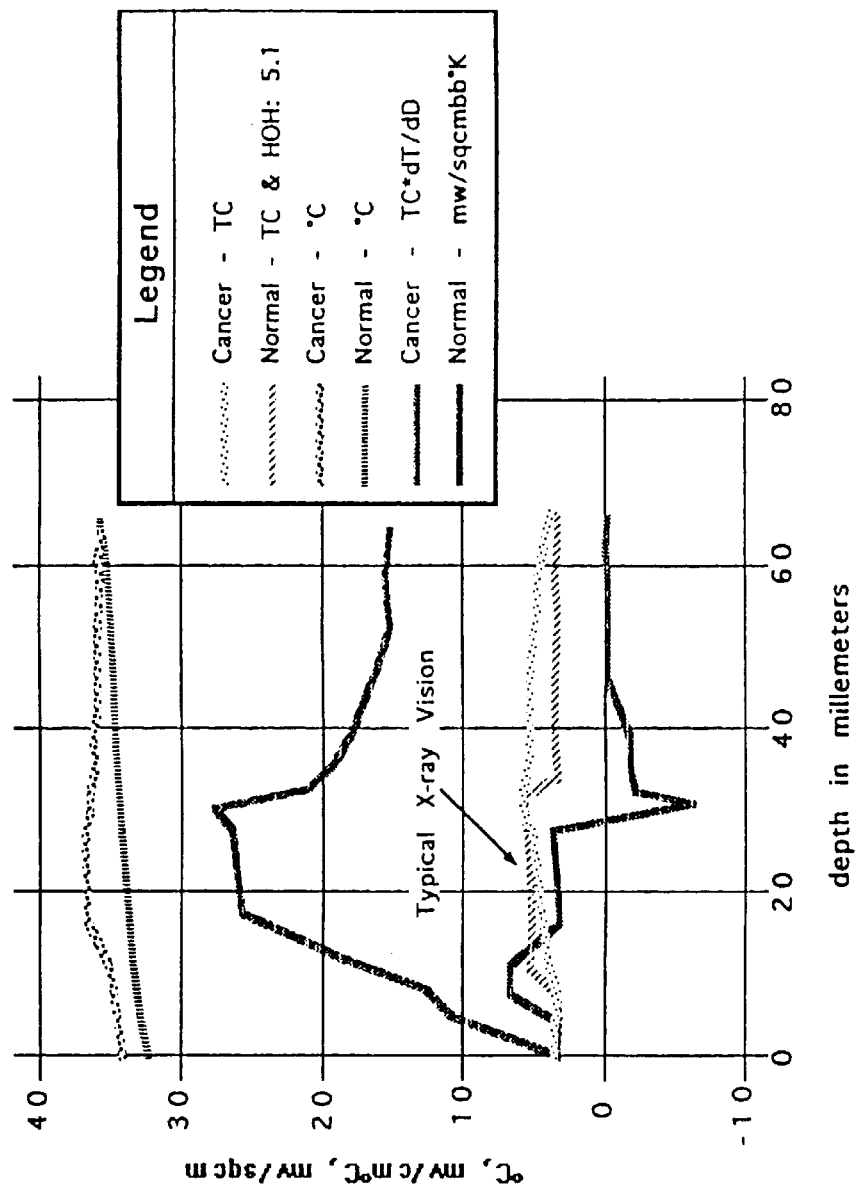
FIG. 3B shows a consolidation of cancer thermal-conductivity analyses of the works of Gautherie, Berger, and others. [Berger 1; and Gautherie 1.]
Figure 3C:
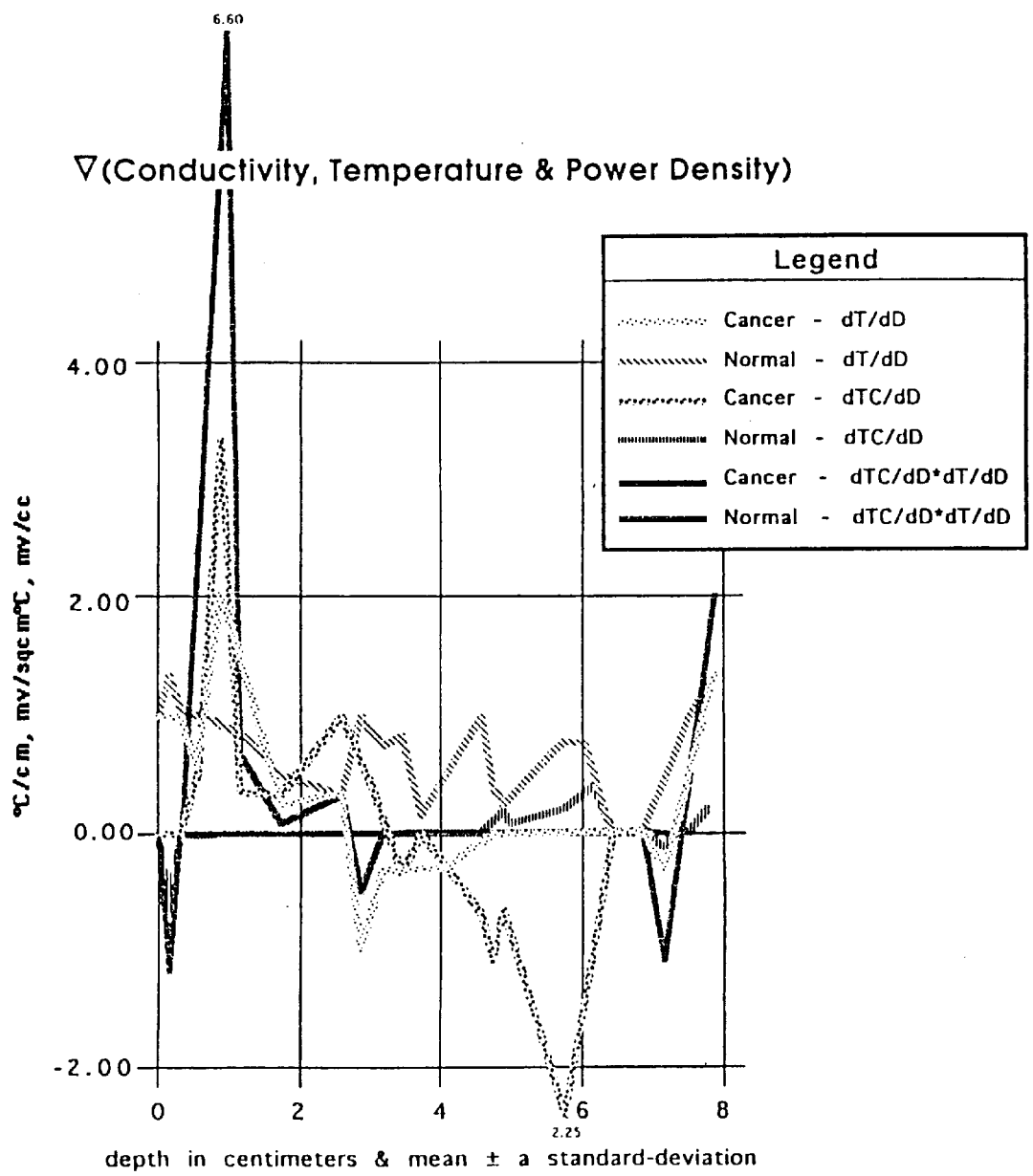
FIG. 3C shows a consolidation of gradients of conductivity, temperature and power density established by the Del-operator ($\nabla$) and derived through the works of Gautherie, Berger, and others. [Berger 1; and Gautherie 1.]

4. Thermal conductivity. Thermal conductivity (3 mw/cm° C.) at skin level is no indicator of cancer. Fact: 5.4 mw/cm° C. inside>>surface. [Berger, et al, 1.] And 2.5 mw/cm° C. for thickening (5 mm) skin cancer that is colder (–2° C.) at surface but hotter in depths>10 mm. Conduction near surface cancers interact with vascular convection from deeper cancers. Fat is more conductive than muscle but less than glands. The assumption that the insulating properties of fat prevent conduction of cancer's heat to skin surface is proven false. [Onai Y, Uchida I, Tomaru T, Irifune T, Yamazaki, Z, and Ohashi Y in a paper entitled "Some Basic Studies on Breast Thermography, Using Phantoms for Detection of Tumors", prepared for the 1968, 1969 or 1970 Conferences on Thermography, and published in *Medical Thermography* by the University of Tokyo Press, Tokyo, Japan, 1973, hereinafter, Onai, et al, 1.] "Thermal conductivity of perfused tissues is confirmed to be significantly higher than that of excised tissues, whatever the histologic type." [Gautherie 1.] For deeply seated cancers, Cooper and Dodd established venous convection as the principal mode of evidence on the skin, i.e., it accentuates venous patterns, whereas, near skin cancers show hot spots. See FIGS. 3A, 3B, 3C and B.

5. 2-dimensional thermography shows contrast confusion. True, but multispectral UV-IR decouples the positional and tonal factors of this confusion, i.e., reflectivity, emissivity, temperature, etc. In addition, transillumination can be used which follows Beer's law with different coefficient than X-rays. X-ray mammography also produces 2-D images without X-ray tomography and it can not in general distinguish between malignant and cystic tumors. The art and science of computer axial tomography is applicable by realtime DSP to "deblur" a depth to focus, assuming some UV-IR penetration and assuming that the cone angle of fibers overlap. The inventors use DSP CAT slices to show coupled Density. "Automated whole-breast scanners may also aid in the diagnosis of masses seen on mammography." [Merritt CRB in a paper entitled "Breast Imaging Techniques" under section name: Imaging the Female Patient and published in *Textbook of Diagnostic Imaging*, by W. B. Saunders Company, Harcourt Brace Jovanovich, Inc., Philadelphia, Pa., 1988, hereinafter, Merritt 1.]

Figure 9:
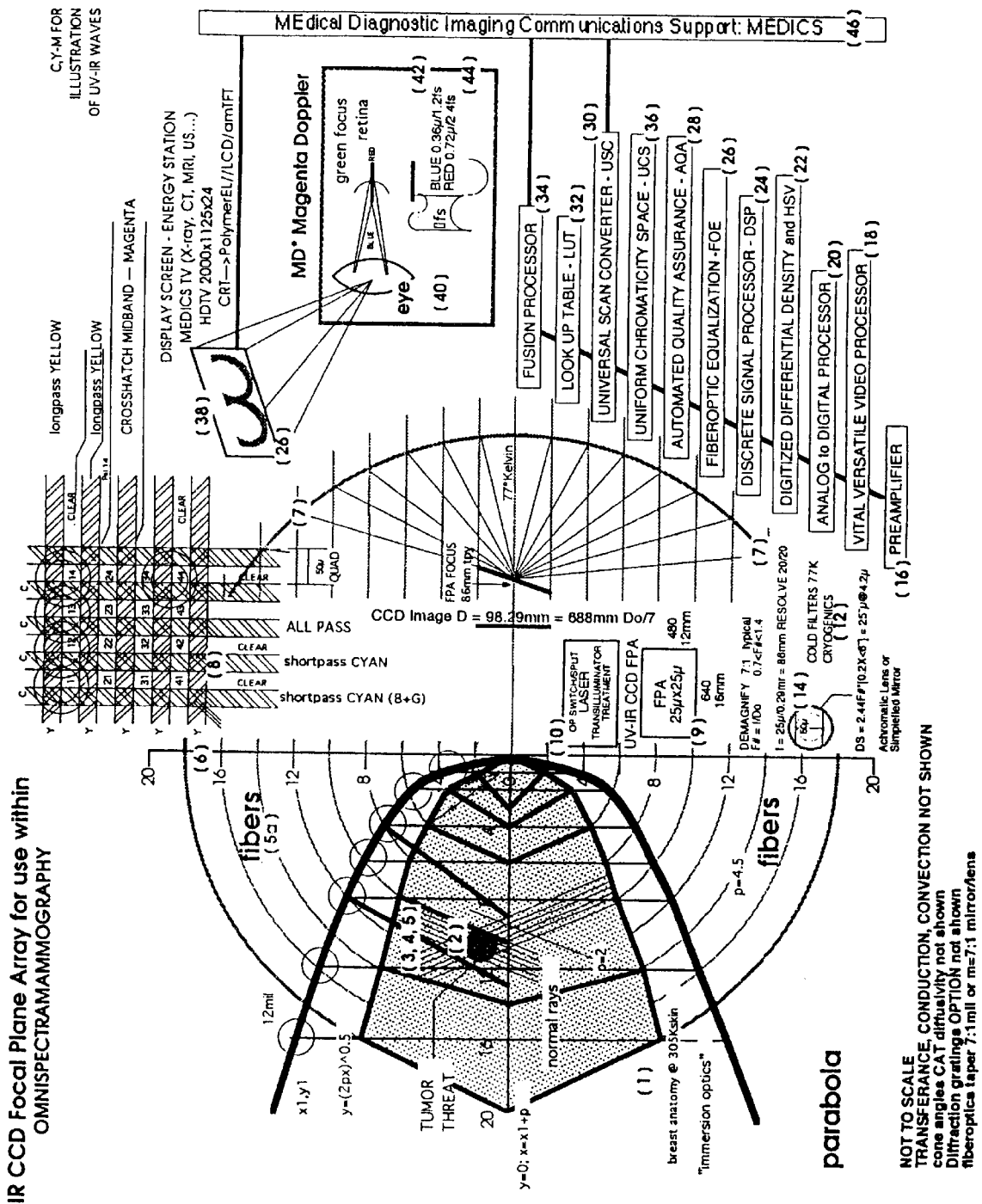
FIG. 9 is a graphic presentation of the IR CCD Focal Plane Array for use within OMNISPECTRAMAMMOGRAPHY and its sensor/display processor, and related applications.

6. Optics. Fiberoptic equalization, first shown and proven at the US Army's MICOM, relaxes the tolerances of imaging devices by computerized automated quality assurance calibration. (The simple CAT scan intent of looking from all angles simultaneously, not in thermography embodiments, minimizes ambient reflection and position errors, as shown in FIG. 9.)

7. Cones. That women's "breasts are bilaterally symmetrical, cone-shaped structures . . . acting as a single organ . . . " [Pope-Jr TL in a paper entitled "Normal Roentgen Anatomy of the Breast" under section name: Imaging the Female Patient and published in *Textbook of*

*Diagnostic Imaging,* by W. B. Saunders Company, Harcourt Brace Jovanovich, Inc., Philadelphia, Pa., 1988, hereinafter, Pope 1.] suggests the more cost-effective conic frustrum than fiberoptic transformer from hemispheroid prompted by definition "breasts are paired, hemispheric structures . . . ". For logical and economical assessment, consider a truncated cone to replace hemispheres of fibers normal to paraboloid cutout. The present invention can make cone and fiber angles the same, that is (for simpler deblur):

$$NA = (1.503329^2 - 1.493318^2)^{0.5}$$
$$= 0.1732$$
$$= \sin(rad/6)$$

For 100% collection, NA=1, each fiber sees 180° full angle ($2\pi$ steradian). A line scan of 640 pixels top(R)-bottom(r), where:

$$r = 480 \times \text{pitch of } 300 \pm 10 \text{ microns}/2\pi$$
$$= 2.292 \text{ cm}.$$

Let height=12 cm, R=4.292 cm. Taper or demagnify the bundle onto the PtSi CCD. Note: Image reconstruction by CPU is dissected from the CCD bundle.

Figure 2:
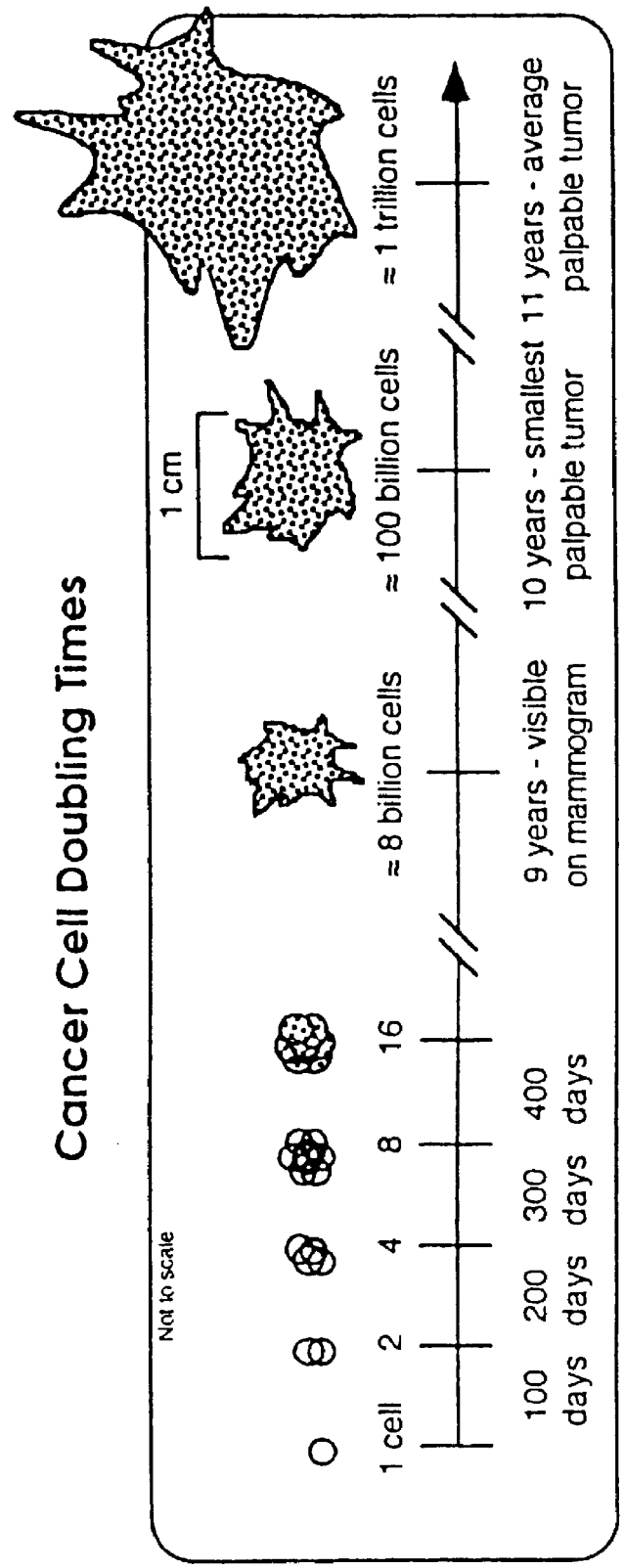
FIG. 2 presents a graphic representation of the breast cancer doubling-times for the average growth form of such cancers and introduces the delay impact of mammographic and palpability detection. [Love S M with Linsey K, *Dr. Susan Love's Breast Book*, A Merloyd Lawrence Book, Addison-Wesley Publishing Company, Inc., Reading, Mass., 1991, 1992, hereinafter, Love 1.]
Figure 4:
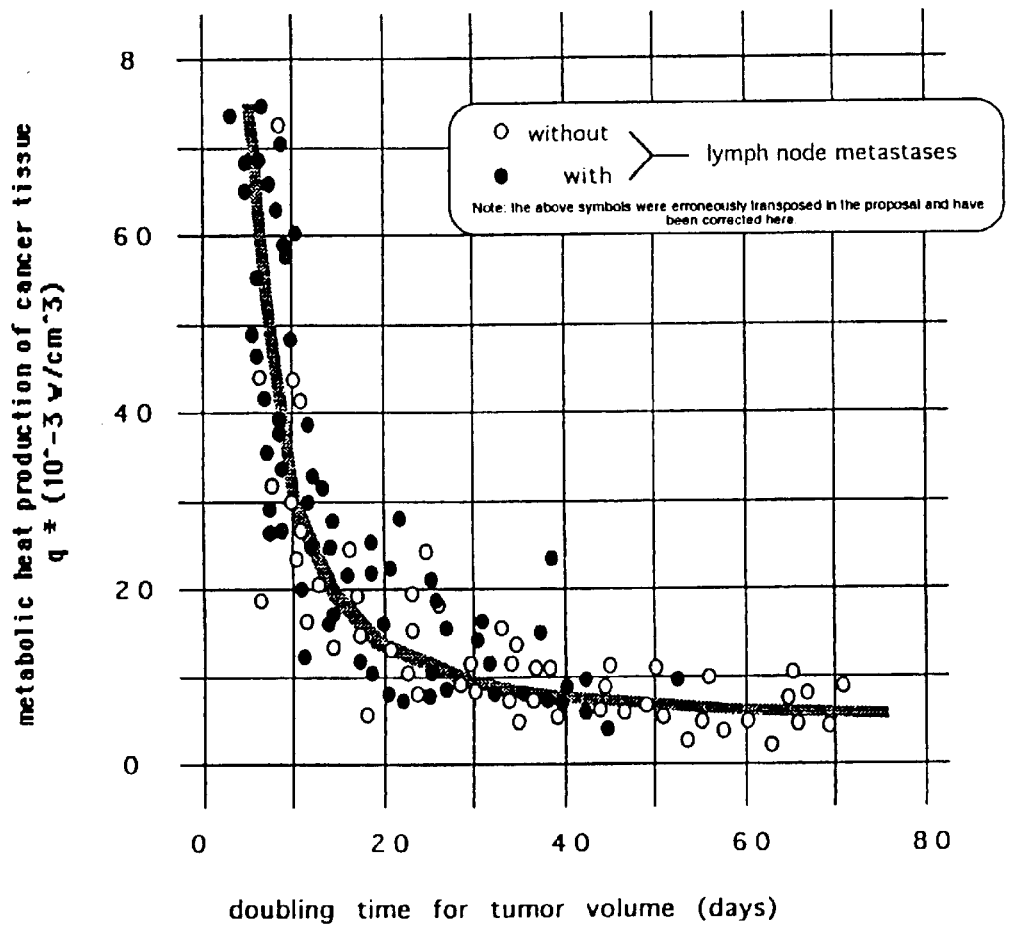
FIG. 4 is a representation of the relationship between the specific heat production of cancer tissue and the doubling of tumor volume versus histologic signs of dissemination. [Gautherie M in a paper entitled "Improved System for the Objective Evaluation of Breast Thermograms", presented to the International Symposium on Biomedical Thermology, Strasbourg, France in 1981, and published in *Progress in Clinical and Biological Research, Volume* 107: *Biomedical Thermology* by Alan R. Liss, Inc. New York, N.Y., 1982, hereinafter, Gautherie 2.]

From standardized thermal diffusion equations and medical data as the constant product of cancer cell doubling-times and power density, it is proposed that a significant improvement in medical detectivity or MD* can be achieved when screening the breast with OMNISPECTRAMAMMOGRAPHY—this is represented as the square-root of the established $2^{27}$–$2^{30}$ cancer cells in its MD* magenta-Doppler. This enables the following detection rate for more vigorous cancer cell growth: (300 days * 12 mw/cc=100 days * 36 mw/cc=30 days * 120 mw/cc). See FIGS. 2 and 4.

Earlier ground noise effects and the so-called 60-cycle-hum produced by power lines limited the image memory sensitivity to a sensor's noise equivalent temperature and its dynamic range of 80 dB. Today, the equivalent is represented by 13–14 bits of graylevel selectively viewed on monochrome monitors with only about 30 dB and 5 bits of capability, or 10 graylevels radical-2 (1.414) times brighter (or denser) than prior gray. Sensor detection of noise equivalent temperature has improved by about a decimal factor per decade since those early results to the current detection range of 0.01° K (Kelvin) or less than 0.01% at 31° K, the body temperature of 98.6° F.

Contrast confusions in the invisible world of ultraviolet-infrared imaging result in the inability to decouple the nonlinear "blackbody" discriminants of spectral wavelength (X), emissivity (e), reflectivity (r), and temperature (T). Current day sensors see integrated irradiance (W), essentially as shown by all or part of the Stefan-Boltzman (sb) equation, i.e., proportional to the fourth power of absolute Kelvin temperature:

$$W_{sb} = (T^4 * (5.679)) \text{ pico-watts/square-centimeter, and}$$

whereas, the Planck peak value (pp) is proportional to the fifth power:

$$W_{pp} = (T^5 * (1.290)) \text{ femto-watts/square-centimeter/micron}.$$

More importantly, the vital Doppler signs or derivatives of these equations, $dW_{sb}$ and $dW_{pp}$, were obscured despite basic calculus:

$$(dW_{sb}/W_{sb}) = ((dT*4)/T), \text{ and } (dW_{pp}/W_{pp}) = ((dT*5)/T).$$

From basic photography, a redefining of display Density (D) equalling $-\text{Log}[V_r]$, so that relative lightness or value ($V_r$) equals the $V/V_{max}$ of passive liquid crystal displays (LCDs) and film, or emissive displays such as cathode ray tubes (CRTs) and electroluminescence (EL), that can all relate directly (1:1) to the above:

$$dT/T \text{ relates to } (dV_r/V_r) = -dDLn10,$$

where a just-noticeable differential Density (jndD) of 0.01=2.3% visibility.

Differential Density is seen linearly, as defined by the Weber-Fechner law, and dHue is seen through Doppler adaptation, but today it is practical to decouple imaging infrared hue, saturation and value (HSV) and, therefore, optimize Planck's blackbody equation and their displays to enhance the engineering sensitivity. The medical detectivity is thereby enhanced through low-cost CLC, at home and personal, and/or through high-definition television at the clinic or hospital, each as a result of OMNISPECTRA-MAMMOGRAPHY (bb):

$$W_{bb} = ((37415 * X^{-5}) * (e(X)))/(\exp(14388/XT) - 1).$$

Just as UV and IR are below and beyond the visible spectra, "ultraX-ray" and "infraX-ray" spectra consist of nuclear gamma rays and several spectral bands beyond the X-ray band. Scattering and absorption coefficients for medical X-rays are well reported but are widely scattered in the literature for UV-IR wavelengths.

Contrary to the manifest myth that heat transfer is only represented in the infrared spectral band, e.g., 8–14 um FLIR or 3–5 um InSb detectors and further, the "Probeye," the electromagnetic spectrum is a continuum of overlapping energy phenomena that interacts observably with invisible body parts of comparable dimensions including cosmic X-rays, for example, of 7.7 micron wavelength, usually associated with the IR of blackbody radiation.

Figure 5:
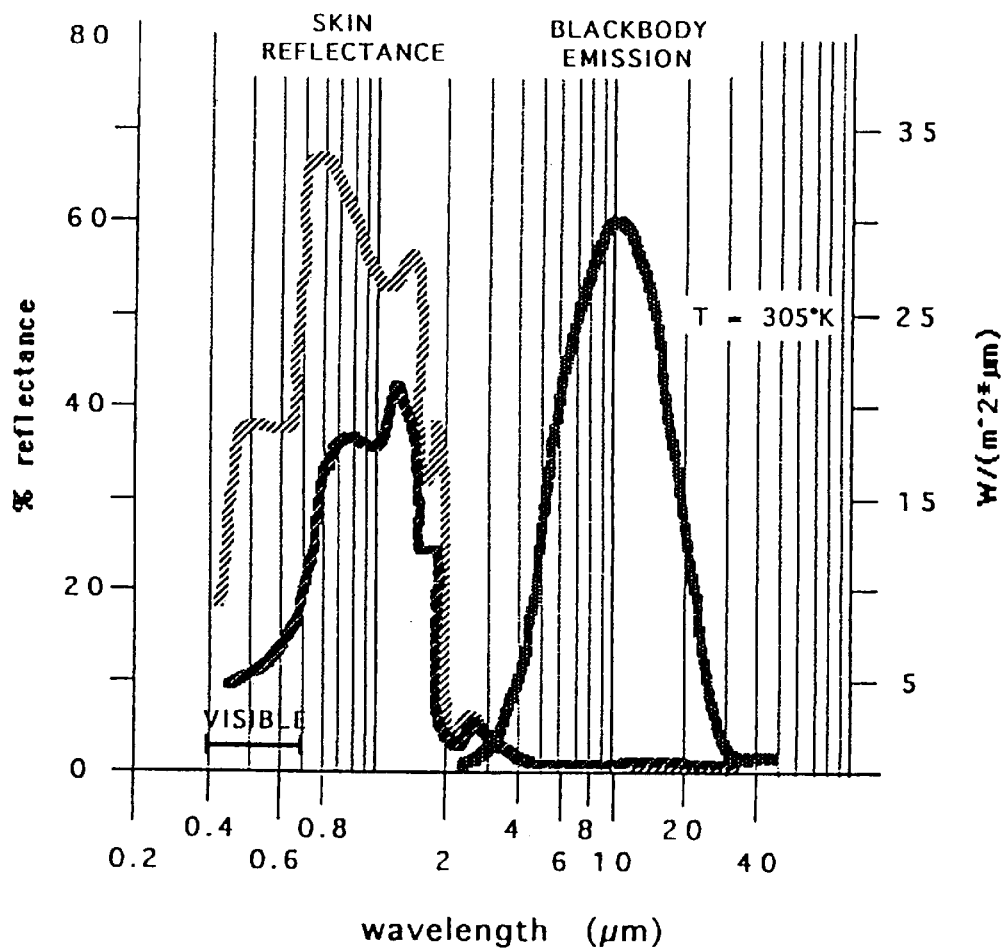
FIG. 5 is a drawing of the spectral reflectance of human skin and the thermal emission spectrum of a blackbody at skin temperature. [Stolwijk J A J in a paper entitled "Evaluation of Surface Temperature Gradients", presented at a June 1975 John Hopkins Hospital seminar on Medical Thermography, and published in *Medical Thermography, Theory and Clinical Applications* by the Brentwood Publishing Corp., Los Angeles, Calif. 1976, hereinafter, Stolwijk 1.]
Figure 6A:
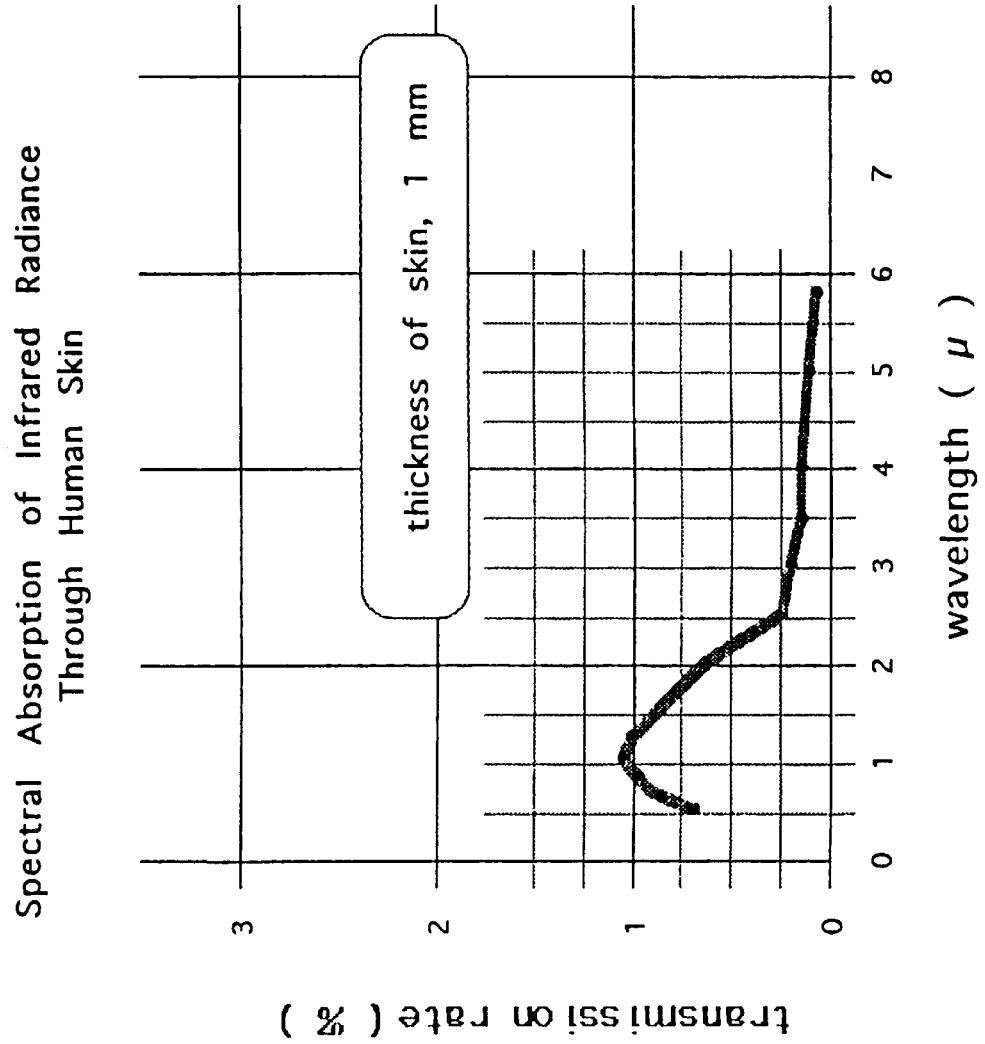
FIG. 6A is a drawing representation of the absorption of infrared light through "almost opaque" human skin. [Fujimasa I, Sakurai Y and Atsumi K in a paper entitled "Some Physical and Psychological Aspects of Thermography", prepared for the 1968, 1969 or 1970 Conferences on Thermography, and published in *Medical Thermography* by the University of Tokyo Press, Tokyo, Japan, 1973, hereinafter, Fujimasa, et al, 1; and Hardy 1.]
Figure 6B:
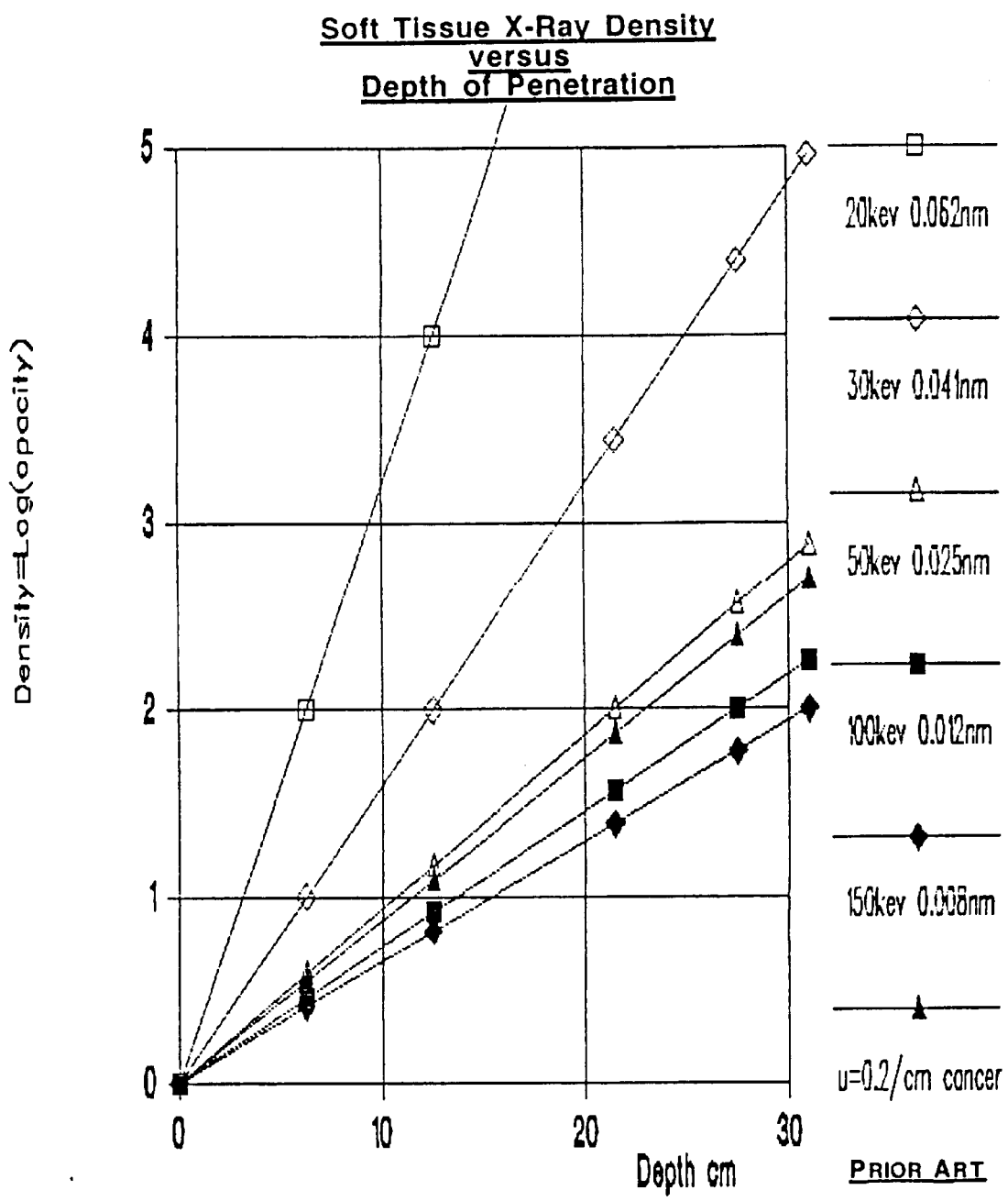
FIG. 6B is a plot of soft tissue X-ray density versus depth of penetration.
Figure 6C:
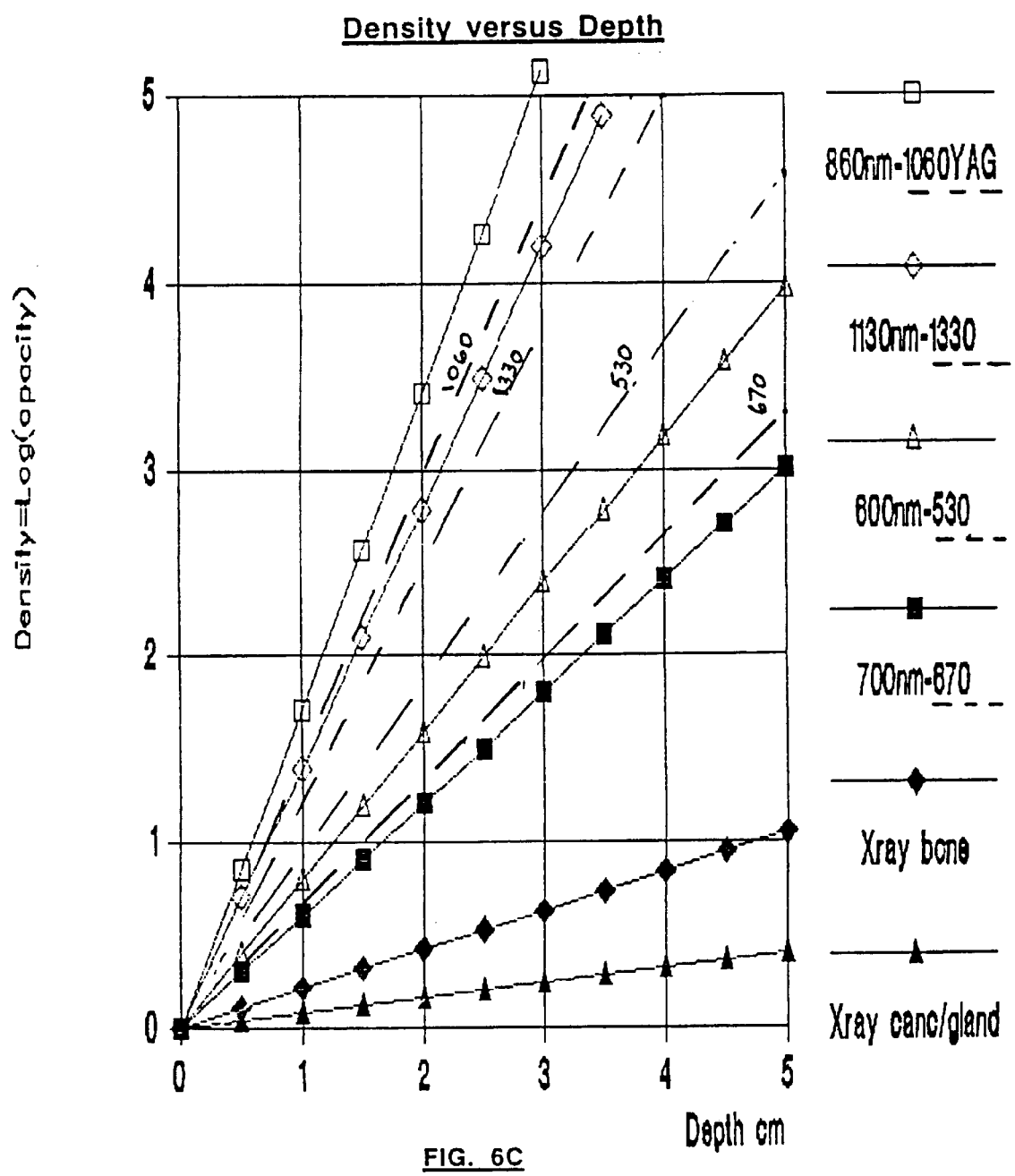
FIG. 6C is a plot of density versus depth for opacity at several X-ray, visible and IR wavelengths.

The UV-IR fusion will reduce confusion of scatterers which will first deconvolve, decompose or deduce from the surface sum of UV-IR rays from subsurface isotropic point sources and from the smaller or larger molecules and particles which cause Rayleigh or Mie scattering respectively. UV for example may exhibit resonance or absorption in 0.03–0.05 micron intracellular structures, called synaptic vesicles, which are reported to contain 5,000 to 10,000 molecules of ACh [acetylcholine]. FIGS. 5 and 6 shows typical spectral response without molecular absorption lines.

Muscle nerve fibers are classified with diameters in the near, mid- and far-IR, that is, 1–6 u, 6–12 u, & 12–21 u. Fortunately, the realtime hardware histograms of AQA are identical to those histograms of fiber diameters from 1–12 um [Kimura J, *Electrodiagnisis in Diseases of Nerve and Muscle: Principles and Practices,* F. A. Davis, Philadelphia, Pa. 1987, hereinafter, Kimura 1.] in the sense of manifestly bimodal distributions and abnormal unimodal.

Imaging spectroscopy may show how the ionized calcium [Ca++] is released into the sarcoplasm, the semifluid plasma which is the intracellular content of a muscle fiber, and, therefore, show how calcium deposits link to breast cancer. [Harris J R, Lippman M E, Veronsesi U and Willett W in an article entitled "Breast Cancer (Part 2)" and published in the *New England Journal of Medicine,* 1992, hereinafter, Harris 1.] Fast muscles tend to be white and are intermixed with slow muscles that tend to be deeper red due to higher myoglobin content.

A muscle fiber, the smallest anatomic unit capable of contraction, averages 50 um in an adult and 10 um in a newborn. The nerve conduction velocity of 40–60 meters/second is coupled to thermal conductivity in terms of 5%/°C. over a range of 29–38° C. "There is a linear correlation between skin temperature and subcutaneous and intramuscular temperatures," [Bosch EP as quoted within Kimura 1, below, 1987, hereinafter, Bosch 1.] which is a good basis for comparison of the normal breast from significant temperature gradient and nonuniform thermal conductivity of cancer cells. (Gautherie 2.]

The unfactored product of scattering (and absorption) coefficients and X-ray range (depth) causes the tonal and positional confusion that can be eliminated by fusion of multispectral modalities that decouple depth and density. Atmospheric modeling, e.g., LOWTRAN programs, can be adapted to the thermal scattering, absorption and transference of the anatomy. The ratio of wavelength of X-ray (X). UV, IR, MRI, ultrasound, etc., to the diameter of scattering particles' cross section circumference ($C=\pi^*$diameter) determines the types of attenuation exponents and "transferance" function through range r, $$T(r,s)=\exp(-r^*Sum(s))$$

for example, $$2\%=\exp(-3.912)$$

Taking natural Loge ($T(r,s)$):

$$Ln(Transferance)=r^*Sum(s)$$

In film:

$$Transferance=1/Opacity=10^{-Density}$$

$$Ln(Transferance\ of\ film)=-Ln10^*\ Log\ (T(r,s))$$

$$Ln(Transferance)=-2.3^*Density(of\ film)$$

Thus:

$$Sum(s)=2.3^*Density/range\ (or\ depth)$$

We see dD per Weber-Fechner law:

$$dD^*Ln10=-dT(r,s)/T(r,s)$$

For the small circumference of molecular particles, $C<X$, and Rayleigh scattering coefficient, $s(Ray)$, varies with $X^{-4}$:

$$\begin{aligned}s(Ray) &= 0.827N^*Ap^3X^{-4}\\ &= 0.827E+9^*(1E-6)^{3*}(1E-3\ cmIR)^{-4}\\ &= 827\end{aligned}$$

where N particles per volume cc, e.g., $23^{30}=10^9$ cancer cells/cc, Ap area particle cross section in cm, e.g., $(0.001\ cm)^2$, air: C<<visible X blue 380 nm<<X red 760 nm<3 u IR s(blue) 0.055 km$^{-1}$=$2^{4*}$ s(red)=$8^4$ s(3 u) . . . Rayleigh.

For larger particles, $2X<C$, Mie scattering coefficient varies with $X^{-0.4}$: in air [RCA e/o]: for example, $$2^*4\ um\ IR<2^*12\ um\ IR\ <C=10\ um\ diameter\ ^*\pi$$

in haze: for example, $$(4\ u)\ 0.50/3^432\ 0.00625\ s(12)$$

$$s(Mie)=[3.9/R\ (km)]^*\ [Xum/0.55]^{-0.585R^{1/3}}$$

Recall:

$$R=visibility\ Range\ \exp(-Rs)=0.02=\exp-3.9$$

A perfectly reflecting, ideal sphere, which is large compared to the wavelength, scatters an incident plane wave isotropically. The "cross-section" is the hypothetical area normal to incident radiation that would geometrically intercept the total amount of radiation actually scattered. Equivalently, the cross section area of an isotropic scattering sphere would scatter the same amount of power as the actual particle. This gives same radiant intensity in a specified direction as does the obstacle, if the extracted power were redistributed isotropically.

For $X<<C$, large scatter cross sections $=\pi^*\ Area^2$ (independent of X). For $X>C$, small scatterer cross sections $=\pi^*\ Area^2/(X/2)^{2-}$ Accordingly, the 2% "visibility range" limits the just noticeable differential Density: jndD=0.02/2.3=0.008686, or say 0.01 of the mind's eye response that is reasonably linear with differential Density, as mentioned earlier.

Because radiologists detect signals below noise and have more sensitivity than the 2% visibility threshold of meteorologists, e.g., 3.5 D/$2^{12}$ (2)=0.00085=jndD/10 max, we draft for the radiologist's consideration their 12-bit sensitivity to expand the international meteorologists 10 definitions of conditions of visibility range in terms of 50–0.0001 centimeters rather than 50–0.05 kilometers, assuming for the moment, multimodal scattering coefficients in cm$^{-1}$.

For example, the "standard clear atmosphere" of 23.5 km may become our "standard clear anatomy" of 23.5 cm=9.25" and the 0.05 km (cm) dense limit would be further divided to see a minimum range below 0.001 cm=10 micron cancer cell.

Alternatively since least significant bits of 12 are reported below the average noise, 2%/4=0.5% might better approximate the doctors' reliable just noticeable difference and associated anatomical scatter coefficients.

The dynamic range of the medical imaging requirement is comparable to that of military Omnispectravision. The $10^{12}$ ratio of IR background radiance (40 mw/sqcm in 3–5 u) to the target NEI (Noise Equivalent Irradiance) of 40 fw/sqcm needed for timely detection and acceptable false alarm rates is about 100 times greater than sunlight to low starlight, and a billion times greater than the display and the eyes' instantaneous dynamic range. The percentage of nominal 300° K blackbody ambient radiation [46 mw/sqcm] within the pre-assigned IR bands, respectively, is<$10^{-7}$%, 1.29%, and 26.35%. A solution to pollution clutter is critical and highly probable in video mixer fusion.

Remarkably, Omnispectravision converts seemingly opaque notch filters, due to line-spectra absorption and scatterings within atmospheric windows, into optimal spike signals produced by the resonance of the object's emissions with the atmosphere's molecular vibrations, for example, with water (HOH) and carbon dioxide (OCO).

Similarly, by fusion of the principles of magnetic resonance imaging at the optical frequencies, mulitspectral transreflective transillumination and narrowband color ratios provide vision of invisible observables of energy densities and diffusivity through the otherwise opaque tissue present in breast anatomy. See FIG. 6B and FIG. 6C.

The gradient of the scalar quantity Temperature, $\nabla T$, is its maximum space-rate of change, a vector quantity in the direction in which the Temperature, $T(x,y,z,t)$, changes most rapidly. $\nabla T(x,y,z,t)=XdT/dx+YdT/dy+ZdT/Dz$, where X, Y, and Z are the unit vectors in respective x,y, and z coordinates. See FIG. 3C.

The $\nabla^*(\nabla T)$ "divergence" of Temperature gradient, $\nabla T$, is called the Laplacian operator, $\nabla^2T$, which is the second spatial derivative that represents the net outward flow per unit volume of the thermal gradient. $\nabla*(\nabla T)=\nabla^2 T=d^2T/dx^2+d^2T/dy^2+d^2T/dz^2$.

The time-rate of change of Temperature, dT/dt, is proportional to this $\nabla^2 T$, such that for the Diffusivity constant, D, $dT/dt=D*\nabla^2 T$ for T=T(x,y,z,t) at time, t, and position, x,y,z. Diffusivity, D, has dimensions of area/time and length*velocity, D=K/[cm/v], where K=thermal conductivity in (mw/sqcm)/(C/cm)=mw/cmC, c=specific heat in j/gmC, C=Celsius temperature, and m/v=mass/volume=specific gravity in gm/cm$^3$.

For arbitrary volume, v, within breast anatomy and its surface area, A, the total flux of heat per unit of time, entering/leaving (+/−) A, is $\iint A(+/-)K\nabla T*ndA=\iiint_v \nabla*(K\nabla T)dv$. Also, the volume integral of a gradient equals the surface area integral of that scalar, $\iiint_v \nabla Tdv=\iint_A TdA$.

Heat energy (joules) in volume, v, is $E=\iiint_v c(m/v)Tdv$.

Power (watts) is $P=dE/dt=d[\iiint_v c(m/v)Tdv]dt=\iiint_v c(m/v)(dT/dt)dv$.

K is relatively constant, near 3 mw/cmC, throughout normal breast tissue, so $\nabla K=0$, but K almost doubles in the vicinity of atypical cells so its gradient and divergence are significant: $\nabla(KT)=K\nabla T+T\nabla K$ for atypical, not constant K. $\nabla(KT)=K\nabla T+T\nabla K$ for normal, and $\nabla K=0$.

$\nabla K \times \nabla T$ gives the power density, P/v, which is inversely proportional to the doubling times of cancer cell growth. Simplifying 3D to one dimension range, r, of needle measurements (depth): $dK/dr*dT/dr=dP/dv=[\iiint_v c(m/v)dT/dt)dv]/\iiint_v dv$.

Dimensionally, [(mw/cm$^2$)/(C/cm)]/cm*C/cm=mw/cm$^3$. For detection, it is not as simple to see all the equations at work, but 3D re-presentations and the magenta-Doppler scientific visualization of infinitesimal differences from the so called "steady state" is simpler in real-time for: $dT/dt=0=\nabla^2 T$.

The fourth spatial derivative is termed the Del-4 operator for point-source extraction of video, being a binary simplification of the biharmonic operator in mechanics. It is a #, 3×3 array, weighted 1-center,=¼-corners, and −½ at NSEW neighbors. The objective function is to minimize NEI, subject to the focal length (f) and detector size (a=w*h) for the required angular resolutions, azimuth "pan", dZ=w/f, and "tilt" Elevation, dE=h/f. The Elevation field of view (NdE) determined discrete number of detectors N; the azimuth FOV and pan [FOR] and scan rate dZ/dt determined the bandwidth B=dt/2, on the order 10$^4$. Hz versus 60 Hz CCD.

NEI minimization is determined by the optics' aperture (A=D$^2\pi$/4) and transmission (T$_x$), detector Detectivity (D$_x$*), area (a) and electronic bandwidth (B), which produce a signal-to-noise=1. Therefore: NEI=$\sqrt{(aB)}/D_x*A T_x)=\sqrt{B}/(A T_x)=4f\sqrt{(dE*dZ/dt)}/D^2\pi D_x*T_x)$. See FIG. 9.

System shot noise is $i_s=\sqrt{(2e i B)}$ and Johnson noise $i_j=(\sqrt{4kTBR})/R$ should be at the background or detector noise limit rather than at preamp noise (i/C) limit as typical TV and many FLIR. Although conventional InSb D$_x$* is near 10$^{11}$ with 25%–60% quantum efficiency in 3–5.5 u, sensor signal to noise ratio can be inferior to FPA/CCD of 0.5% QE at 4 u because it's inversely proportional to Capacitance (C), and CCD 36 femtofarad is orders of magnitude better, as is the FPA exposure time, dt*NEI=NEE. CCD e=(36 ffd)(4.5 uv); 765 mv/170 ke at 40 Mphot=2pj.

"Prewhitening" RC circuits typically compensated 1/f low-frequency noise but now, preferably, direct coupled digital FOE/AQA employs spatial/temporal filters to enhance pixel uniformity and the eyes' tuned sensitivities.

By definition, the "matched filter" maximizes the signal to mean-square-noise ratio—whether the cancerous growth subtends less than one pixel of total field of view. Median filters which replace central pixel gray values by the median of the surrounding 3×3, 5×5, etc., have been shown by Parenti and Narenda to be more effective because the noise is not Gaussian and the median value, not mean value, minimizes the expected absolute deviation as well as the impact of impulse spikes. Longpass/shortpass filters match the predominant anatomic windows at photopic octaves.

IR "jargon" is the worst laboratory-to-user obstacle, e.g., (mw/sqcm)°K/cm, Cal/hr/°K/cm, (Btu/hr)/sqft°F/Ft, Cal cm/s sqcm°K, etc., so for new readers tempted to say "it's Greek to me", the E, Z, and X font replaces phi, theta, lambda. Newton's notion of "visual vibrations" for diffraction optics' chromatic adaptation, corrects the so called "aberration" in the mind's MD* magenta-Doppler.

When you're expanding 20/20 vision [arc minute resolution=291 urad=25 um/85.9 mm] capability to unweave the rainbow in space-time-spectra [1–5 u is good but UV-5.5 u is awesome] to see impact of thermal gradients and thermal conductivity through "opaque" media, multi-layer surfaces, anatomic scatterers, minimum resolvable temperatures take on new dimensions. MIL/MED Fusion energy>>sum of parts!

The end goal of this task is to develop optimum multicolor UV-IR sensor/display technology for multimode fusion of data.

Figure 7:
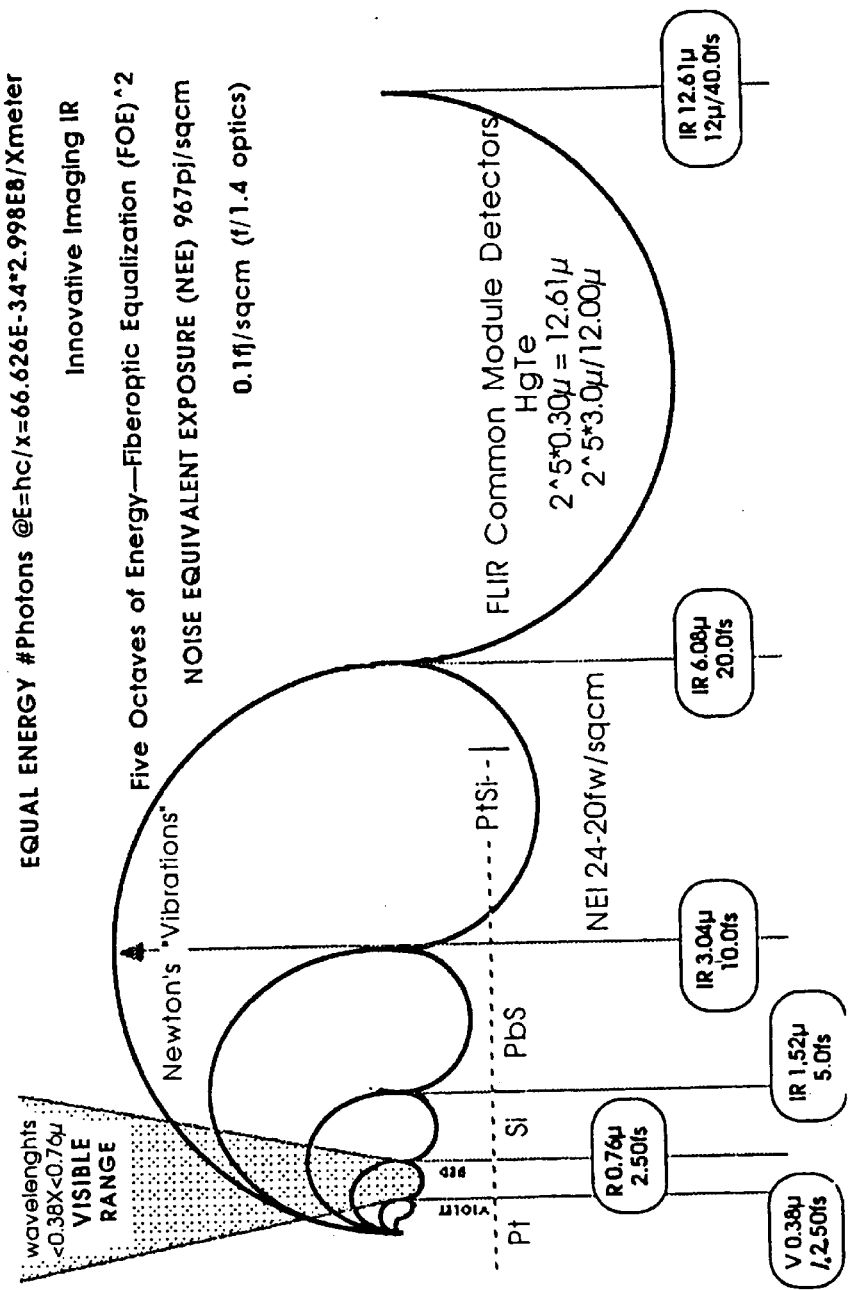
FIG. 7 is a graphic presentation of the wavelength range of radiologic analysis represented within this invention.
Figure 8:
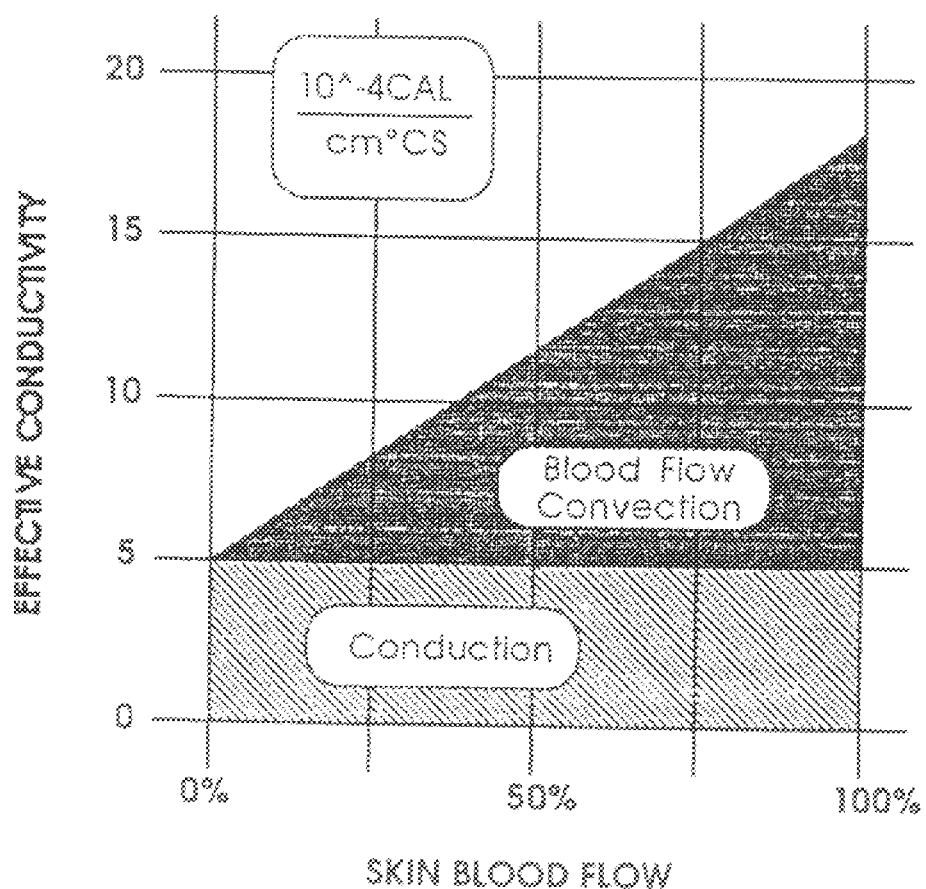
FIG. 8 is a representative drawing showing the "effective thermal conductivity" of the skin being increased relative to blood flow. [Dittmar A, Marichy J, Grippari J L, Delhomme G and Roussel B in a paper entitled "Measurement by Heat Clearance of Skin Blood Flow of Healthy, Burned and Grafted Skin", presented to the International Symposium on Biomedical Thermology, Strasbourg, France in 1981, and published in *Progress in Clinical and Biological Research, Volume* 107: *Biomedical Thermology* by Alan R. Liss, Inc. New York, N.Y., 1982, hereinafter, Dittmar 1.]

The intent is spectral filtering and fusion of signals within five octaves of visible energy that have been processed from as little as possible to maximum effective use of vision-computers, as shown in FIG. 7.

To wit opacity is half the secret of success! As the Army NVL probably knows best, the difference or derivative of Log of opacity defined as the reciprocal of transmittance or transmission, conforms closely to the often forgotten Weber-Fechner law of psychophysics.

Compare Army MDIS X-ray to IR; NEE versus NET, NEI: Recall D=Log[1/T] but detect/digitize/display dD=[dT/T]/Ln10 over the full useful or instant dynamic range $D_{max}-D_{min}$, e.g., 3.5/2[$^{8, 10 \text{ or } 12 \text{ bit}}$]Kodak Xray film, where average noise is equivalent to 4–16 dD's of 10–12 bit A/D. Ten bits of gray only provides 0.1% quantizing at full scale transmission but "down in the mud" dT/T, which we see, often is worse than 4–5 bits of digitized differential Density (dD). For active and transreflective displays we define D=Log[Relative Brightness].

A practical understanding of the Weber-Fechner law of vision and utilization of differential densities within a total image process model will improve the multimedia matching of the nonlinear man/machine "visibility" of both contrast limits and) and resolution limits (Modulation Transfer Function). It also proposes to gamma- correct IR-imaging and LLLTV input/output e/o devices so that the eve-brain's sensitivity to differential densities is made proportional to the properly digitized scene parameters via comprehensive and consistent full color to minimize metamerism.

AQA calibrates the sensor/display automatically by the CPU commanding specific reference gray and color levels, reading-the fiberoptic feedback signals, generating the appropriate control to zero the error signal, computing the offset hue, saturation and values of brightness, contrast gain, and gamma correction, then writing the transformation values to RAM look-up table (LUT) at each level location to be addressed in realtime by each digital value of input video. The same digital image data will then produce the same dependable display contrast and color anywhere, anytime on any tube or flat panel display, such as the display screen set forth in U.S. Pat. No. 5,019,807, the disclosure of which is incorporated herein by reference.

Apparent sensor/display discrepancies in semantics, specmanship, or technical Jargon can be resolved for example when one claims only ten gray levels, another 32, and another 256 for the same display monitor. Ten standard (EIA) gray steps, radical two darker than the previous, is equivalent to ten steps of differential density (dD=0.15) and this is also equivalent to five steps, two times darker, i.e., $2^5$=32. However, the dD of 0.15 is equivalent to 3 db which is easily and comfortably discriminated, whereas, the just-noticeable- difference is defined at 50% probability of detection where half the viewers see a difference, e.g., 2% visibility near jndD=0.01. Since each binary bit is equivalent to 0.3 dD or 6 db, then over the 30 db dynamic range of 1.5 $D_{max}$ of 32 linear levels, most if not all 256 gray levels can be discerned, especially within local areas. For hue and saturation, $du, dv < 2^{-7}$ in uniform chromaticity space UCS.

The perennial problem is that the least significant bit (LSB), e.g., $0.39\% = 2^{-8}$ of full scale, has variable effect at different brightness levels, whereas the eye-brain visionics responds more linearly to differential Density or the contrast ratio $dV_r V_r$, where $V_r$ is the relative value of brightness divided by maximum brightness. Now this relative value brightness $V_r$ is equivalent to film transmission or paper reflectance, such that $-Log(V_r)$ is defined as Density and thus: $dV_r V_r = -dD \, Ln10$; $V_r = 10^{-D}$; $2.0\% = (0.0087) \times 2.3 = $jnd contrast "visibility"; and 2.0–2.5%=MTF @1'->40% @2'. Notwithstanding nonlinear inputs and CRT nonlinearity, sensor/display processor AQA LUT transforms discrete steps to differential color densities with proven response over full dynamic range. Once the full range of brightness is transformed for monochrome, a similar transformation LUT technique in uniform chromaticity space renders proportional responses to $0.01^3$ jnd's in HSV coordinates, as well as, RGB, UCS or CIE space and FPA spectral filters.

Present day technology represented by fiberoptic feedback and Doppler radar (or Doppler radiography) can in fact detect miniscule differentials in signal intensity, as will multi-color infrared MD* magenta-Doppler imagery with a $2^{18}$–$2^{24}$ dynamic range in sensitivity and dependability. Miniscule changes in breast and pectoral lymph node anatomy, on the order of 80 femto-watts per pixel, can be seen through newer infrared, multi-color/multi-source charge coupled discrete TV cameras (the charge coupled device to be employed within this approach is in fact a high-performance charge coupled discrete TV camera employing a platinum silicide chip developed for infrared image processing within the military) working with low-cost, bra-like, fiberoptic feedback capabilities (the fibers used in this feedback system are advanced infrared fibers, e.g., KRS), even at home on an everyday television monitor. Its fiberoptic bezel provides quality control feedback from the breast anatomy, calibrated such that the same digital data subsequently produces an identical display, on any display device. The three unknowns of radiation (wavelength), emissivity, and temperature are solved by nonlinear equations, transforming them to the easily recognized and understood (optimal mapping of) perceptual conditions of hue, saturation, and value, respectively. This is adaptive thermal vision, seeing and displaying the conditions of breast anatomy, as shown in FIG. 9.

The medical community can precisely measure the improvements in breast anatomy change detection, demonstrated with this adaptive thermal vision and its conservative 16–1000 times enhancement in sensitivity. As indicated above, thermal diffusivity suggests significantly quicker (earlier) medical detectivity levels, and automated quality assurance and newer multi-discriminant processor features provide "a concurrence of evidence" regarding all the diagnostic data gathered during the process. That is, vision of the invisible observables in the 310 micron pixel range, within 15 cancer cell doubling-times from inception and with far less 3D confusions, is a realistic postulate with OMNISPECTRAMAMMOGRAPHY.

This display begins to articulate the OMNISPECTRAMAMMOGRAPHY technology of combining, that is, intertwining or threading, cancer thermodynamics with Maxwell's "mental science" of color, a process characterized as MD* magenta Doppler, to enlighten or see heat transfer by radiation, conduction and convection. In doing so, magenta Doppler, through modern multimodal medical imaging, provides a medical screening environment for early cancer detection-an early warning systems, as it were, for breast cancer detection.

Magenta Doppler portrays easy-to-see, comprehensive and consistent color through the use of advanced single-microchip integrated circuit (1-IC) technology in order to optimize the vision of the invisible observables, over a five octave range of spatial frequency. This is accomplished through the focal plane fusion of charge coupled discrete Doppler derivatives, density and depth—not false color thermography. The radiometrics and derivative nature of color depth in radiography renders MD*, for early screening of breast cancer, as a visual analog to the audible pitch warning of a siren. The novel output of the CCD transforms input opacity to photons into optical density within the FPA (focal plane array). Effectively, this presents-again the fusion or integration—the "concurrence of evidence"—of infinitesimal percentages of spectral exitance [dW/W], thermal gradients [dT/T], conductivity, diffusivity, and/or wavelength [dX/X], due to the natural logarithm ln/W/, which= Integral [dW/W].

Magenta Doppler is simply the most magnificent color for the visualization of the minute separation of variables, such as the bundled XT WaveTemp lumped-parameter used to simplify its mathematics. (See the WaveTemp table below.) To "unweave the rainbow" and eliminate contrast confusion, consider the ratio of Planck/peak(Wein) blackbody spectral radiance in terms of the old single parameter, XT, and define the slope anew as:

$$m = C_2/XT$$
$$= [dW/W]/[dT/T]$$

The Wein law says $W_{peak} = [1.29 \text{ fw/sqcm}/\mu]^* T^5$ at XT=2898 $\mu$K; so, dividing it into Planck's blackbody equation gives percent peak.

$$W/W_{peak} = [3.74E - 12W\text{sqcm}/1.29E - 15W\text{sqcm}]/[(XT)^5(e^m - 1)]$$
$$= 0.2898/[(XT)^5(e^m - 1)]$$
$$= 1$$
$$\text{for } m = C_2/XT$$
$$= 1.4388/0.2898$$

For m=4.96, the −1 can be neglected with less than 1 percent error to simplify the calculus of variations below XT=2898:

$$dW/W = m \, dT/T$$
$$= (m - 5)dX/X \text{ so that}$$

-continued
$$dT/dX = (T/X)[1 - 5/m] \text{ and}$$

$$dT/T = [1 - 5/m]dX/X.$$

As Lambertian source, spectral radiance $W/\pi = L$ in $W/sqcm/sr/\mu$ becomes, in terms of $w/sqcm/sr/Hz$:

$$L_f = 2hc/[X^* X^2(e^m - 1)]$$
$$= [2kT/X^2]^*[m/(e^m - 1)].$$

Rayleigh-Jeans $L_{RJ} = 2kT/X^2$; $hc/X \ll kT$, i.e., $C_2/XT < 0.1$ and <5% err, e.g., the sun at $5,900°K > 24\mu$, is beyond the present scope of PtSi CCDs but sunlight or room be ignored.

Also, the ratio of Planck's [N photons per second] divided by Stefan-Boltzman [$N_x/W_{SB}$]:

|  |  |
|---|---|
| | = [W/π/(hc/X)]/Total integral |
| | = TBD/(XT)$^4$(e$^m$ − 1) |
| $(0.3670)^4(e^{3.92} - 1)$ | = 0.8962 |
| | = 0.01814(50.4 − 1) |

| WaveTemp [XT] | (effect) | slope [m] | Wavelength |
|---|---|---|---|
| 1457 μK | (0.25 peak) | 9.90 | 4.80μ*305° K. skin |
| 2100 μK | (0.75 peak) | 6.90 | 6.90μ*305° K. skin |
| 2411 μK | (max dL/dT) | 5.96 | 7.90μ*305° K. skin |
| 2898 μK | (peak & 0.25 total) | 4.96 | 9.50μ*305° K. skin |
| 3670 μK | (max p/s) | 3.90 | 0.62μ*5900° K. solar |
| 4111 μK | (0.50 total) | 3.50 | 0.70μ*5900° K. solar |
| 6200 μK | (0.75 total) | 2.30 | 1.05μ*5900° K. solar |
| 7000 μK | (0.25 peak) | 2.00 | 1.19μ*5900° K. solar |

The inventors envision expanding the visual imagery band (0.38 to 0.76 microns) for fusion and display, and/or the use of alternative sources for the platinum silicide (PtSi) chip to achieve the three-color processing at economies of scale.

The sensor/display processor is comprised of functional blocks shown in FIG. 1 and in greater detail in FIG. 9 where the hardware components as well as software and firmware functions are identified by the numerals, as "[0]" and described.

A plane view sketch of the breast anatomy [1] includes a tumor [2], e.g., in the mammary duct or lobules and normal constituents [3], [4], and [5], e.g., glandular tissues, fatty tissues, veins, etc.

The optical fibers [5a] in bra-like parabolic or spherical structure collect the UV-IR breast emittance and heat transfer from [2] thrrough [3], [4], and [5] by conduction and convection as well as the transferance and reflectance from the transilluminator [10]. The fibers [5a] maybe tapered down, with proper thermal insulation, onto the spectral filters [8] overlaying the focal plane array CCD [9] cooled by cryogenics, [12], e.g., thermoelectric or liquid nitrogen 77°Kelvin.

Alternatively, the fiberoptic plane 6 can be imaged down and demagnified typically 7:1, as shown by a spherical mirror or achromatic lens and cold filtered to minimize background noise from outside the detectors' intended field of view.

Transilluminator [10] consists of an optical switch and laser or narrowband filtered lamp to photogate the FPA CCD [9] which sees both the passive emittance as well as the reflectance and transmittance through the breast anatomy. Therefore, the same low power configuration for detecting the tumor with sensitivity and specificity provides the enabling technology for pinpointing the higher power laser exposure to treat the cancerous cells with preferential absorption from drugs so good cells are not damaged.

The focal length of [7] is chosen to resolve the equivalent of 20/20 vision, i.e. an arc-minute or 0.29 milliradian for example f=86 mm=25 um detector/0.29 mr. The diameter of [7] is maximized to minimize the diffraction limited spot size [14] and NEI, on order of 80 femtowatts per pixel.

Low-noise, preamplifier [16] is well known in art begun with the CCD invention in 1969, however, instead of the typical signal proportional to the media transmission of input photons or irradiance, the present preamplifier connects to the CCD signal and power drain thus provides to the vital versatile video process [18] the preferred voltage output signal proportional to density and thus maintains optimum sensitivity to differential densities over the dynamic range. The input to analog to digital (A/D) processor [20] from [18] is adaptively scaled so as not to saturate the A/D [2] nor lose the small signals in noise.

Digitized signals are calibrated to density and color in terms of [22] hue, saturation and lightness for the DSP [24]. Reference signal conditions are commanded and controlled to measure error signals and thus compensate for nonuniformities of components so that fiberoptic equalization [26] allows larger device tolerances and lower costs through the adaptation of automated quality assurance [28].

Formats for TV and medical imaging are undergoing radical changes such that Universal Scan Conversion [30] accommodates all of them and includes the necessary interpolation/decimation. LUT [32] allows offline mathematical transformation of optimum signalization to be downloaded into random access memory and readout in realtime.

The fusion processor [34] is an expanded adaptation of Omnispectravision to exploit the Uniform Chromaticity Space [36] for stable vision on display screen [38], also with fiberoptic equalization for presentation of magenta Doppler as depicted in the eye [40] as blue [42] bends before the retina and red [44] bends behind the retina such that the mind's eye response to the tumor diffusivity coming or going is analogous to the Doppler shift of star light or Doppler pitch of moving sirens coming and going away, respectively.

In addition, while certain wavelengths for different anatomical conditions have been set forth, they are illustrative and should not be considered exclusive.

Thus the present invention realizes the aforenoted objects, advantages and features, and although preferred embodiments have been disclosed and described in detail herein, its scope should not be limited thereby, rather its scope should be determined by that of the appended claims.

The chart on the following page serves to provide a concise summary of the foregoing.

| Prior Art Modality (limitations) | Specific Advantages | Multimodal Synergism |
|---|---|---|
| In Mammography: | Non-ionizing active/passive sensor/display processor resolving data over a 5-octave UV-IR range | Energy station, establishing concurrence of evidence presented, to reduce computer needle probe data and perform pinpoint biopsies/removals |
| Low contrast in low fat breast tissue, <50 years | | |
| | Subpixel(0.3 mm) imaging | |

-continued

| Prior Art Modality (limitations) | Specific Advantages | Multimodal Synergism |
|---|---|---|
| Detection at 5 mm, but > 10 mm screening in practice | spectroscopy screening ($10\mu^3$ voxel goal) | Low-coat personal screening 1-1C and professional diagnosis |
| Planar view of 3D confusions | Omniview fiberoptic collector and computer tomography UV-IR | Separation of variables and fusion versus confusion of discriminants |
| Exp(-scatter*range)ambiguity or else tomography with its increased radiation levels | Simultaneous equations give multispectral range and optimum wavelengths | |
| | Thermal gradients [Del-1, 2, 4] and divergence of surface and volume integrals | Conformal mapping of spatial and spectral data patterns to discriminate false alarms (+) and minimize false misses (−) |
| In Thermography: | Stable visions of energy density constant rapid doubling times | Thermal IR-UV tomography Automated quality assurance of 100 day*35 mw/cc (average) |
| Planar view of surface temperature of 3D volume | | -milk's metabolic energy- and 30 day* 120 mw/cc (rapid) |
| Red hot, blue cold | Magenta-Doppler diffusivity (conductivity almost doubles that of HOH-more in cancer) | >> Omnispectravision 3–5$\mu$ atmosphere window analogous |
| Venous hot spots divert tumor source | Not pseudo-color: "mental science" true-color vision- | to LOWTRAN program for multi-layers of anatomy background and foreground scattering |
| False positives and negatives | computer "deblurs" depth of focus and cloud of scatters | Doppler-like differencing of growth: red far, blue nearer |
| | Photogated CCD/laser transillumination | 3D 3-color UV-IR deduces confluence of conduction and convection, radiation and transference |
| In Transillumination: | Narrowband, multispectral lamp or laser color ratios of transference | Fiberoptic equalization |
| Broadband lamps inefficient, hot and scatter-like fog | and reflectance and absorption [jnd Density << 0.01 dH*dS*dV < 1 ppm = $10^{-6}$ | Exploit resonance lines to see through "opaque" tissue, UV-IR |
| | Optical resonance images | Observable potential of controllables of pinpointing laser treatment of tumors |
| In Magnetic Resonance Imaging: | Seemingly opaque absorption lines resonate at molecular vibrations, for example, 4.2$\mu$ carbon dioxide and near-IR water | Low-cost 1-1C screen, highly stable, digital discrete color ratios for time-lapse CCD photography, UV-IR Multisignal/noise > 10 may trace deregulated dT and growths to hypothalmus |

I claim:

1. A sensor/display processor comprising:
    a charge transfer device having a focal plane array and a charge;
    a laser or narrowband filtered lamp for photogating said focal plane array of said charge transfer device;
    optical means and spectral filter means to collect and focus photons from anatomy emittance, reflectance and transillumination onto said focal plane array of said charge transfer device;
    video amplifiers and processing means coupled to said charge transfer device to convert a discrete analog transmission signal proportional to said charge to a digital density signal proportional to logarithm of transmission reciprocal or opacity;
    fiberoptic equalization means for automatically compensating with fault-tolerant correction for nonuniformities in the charge transfer device and the optical means and spectral filter means;
    fusion processor means for measuring weighted likelihoods and ratios of multispectral observables to detect cancer with minimum false negatives and false positives; and
    display means having stable vision for displaying invisible observables in optimum color having Uniform Chromaticity Space du, dv less than 0.01, for encoding tumor diffusivity in one color when approaching and in a different color when receding to effect its scientific visualization providing a magenta Doppler.

2. The invention in accordance with claim 1 wherein said optical means comprises optical fibers assembled in a bra-like structure.

3. The invention in accordance with claim 2 wherein said optical fibers further includes an achromatic lens.

4. The invention in accordance with claim 3 wherein said laser or narrowband filtered lamp performs transmissive and transreflective illumination, detection and diagnosis.

5. The invention in accordance with claim 4 which includes magenta Doppler encoding means for detecting cancer diffusivity after minimal doubling times of cancer cell growth.

6. The invention in accordance with claim 2 wherein said optical fibers further includes achromatic reflective optics.

7. The invention in accordance with claim 3 wherein said laser or narrowband filtered lamp performs transmissive and transreflective illumination and treatment.

8. The invention in accordance with claim 1 wherein said optical means comprises an achromatic lens.

9. The invention in accordance with claim 1 wherein said laser or narrowband filtered lamp performs transmissive and transreflective illumination, detection and diagnosis.

10. The invention in accordance with claim 1 which includes magenta Doppler encoding means for detecting cancer diffusivity after minimal doubling times of cancer cell growth.

11. The invention in accordance with claim 1 which further includes vision-computer means for automatically and substantially realtime detection of atypical cell growth by recognition of Doppler-like shifts in color ratios.

12. The invention in accordance with claim 1 wherein said fusion processor means further includes means for conformal mapping and comparisons of multiple modalities of medical imaging.

13. The invention in accordance with claim 1 wherein said optical means comprises achromatic reflective optics.

14. The invention in accordance with claim 1 wherein said laser or narrowband lamp performs transmissive and transreflective illumination and treatment.

* * * * *